(12) United States Patent
Keller et al.

(10) Patent No.: US 10,077,448 B2
(45) Date of Patent: Sep. 18, 2018

(54) METHODS AND SYSTEMS FOR PRODUCING FUNGAL SECONDARY METABOLITES

(71) Applicant: Wisconsin Alumni Research Foundation, Madison, WI (US)

(72) Inventors: Nancy Keller, Madison, WI (US); Philipp Wiemann, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 85 days.

(21) Appl. No.: 15/044,408

(22) Filed: Feb. 16, 2016

(65) Prior Publication Data
US 2016/0237443 A1  Aug. 18, 2016

Related U.S. Application Data

(60) Provisional application No. 62/116,730, filed on Feb. 16, 2015.

(51) Int. Cl.
| | | |
|---|---|---|
| C12N 1/14 | (2006.01) | |
| C12P 17/18 | (2006.01) | |
| C07H 21/04 | (2006.01) | |
| C12N 1/20 | (2006.01) | |
| C12N 15/80 | (2006.01) | |

(52) U.S. Cl.
CPC ............ *C12N 15/80* (2013.01); *C12P 17/181* (2013.01)

(58) Field of Classification Search
None
See application file for complete search history.

(56) References Cited

PUBLICATIONS

Du. Function and regulation of aflJ in the accumulation of aflatoxin early pathway intermediate in Aspergillus flavus. Food Addit Contam. Oct. 2007;24(10):1043-50.*
Yu. Conservation of structure and function of the aflatoxin regulatory gene aflR from Aspergillus nidulans and A. flavus. Curr Genet (1996) 29: 549-555.*

* cited by examiner

*Primary Examiner* — Yong D Pak
(74) *Attorney, Agent, or Firm* — Boyle Fredrickson S.C.

(57) ABSTRACT

The present invention discloses methods and systems for producing fungal secondary metabolites. The invention also discloses genetically modified organisms and kits including such organisms for producing fungal secondary metabolites.

16 Claims, 19 Drawing Sheets
(8 of 19 Drawing Sheet(s) Filed in Color)
Specification includes a Sequence Listing.

A. nidulans WT

A. nidulans TPMW2.3

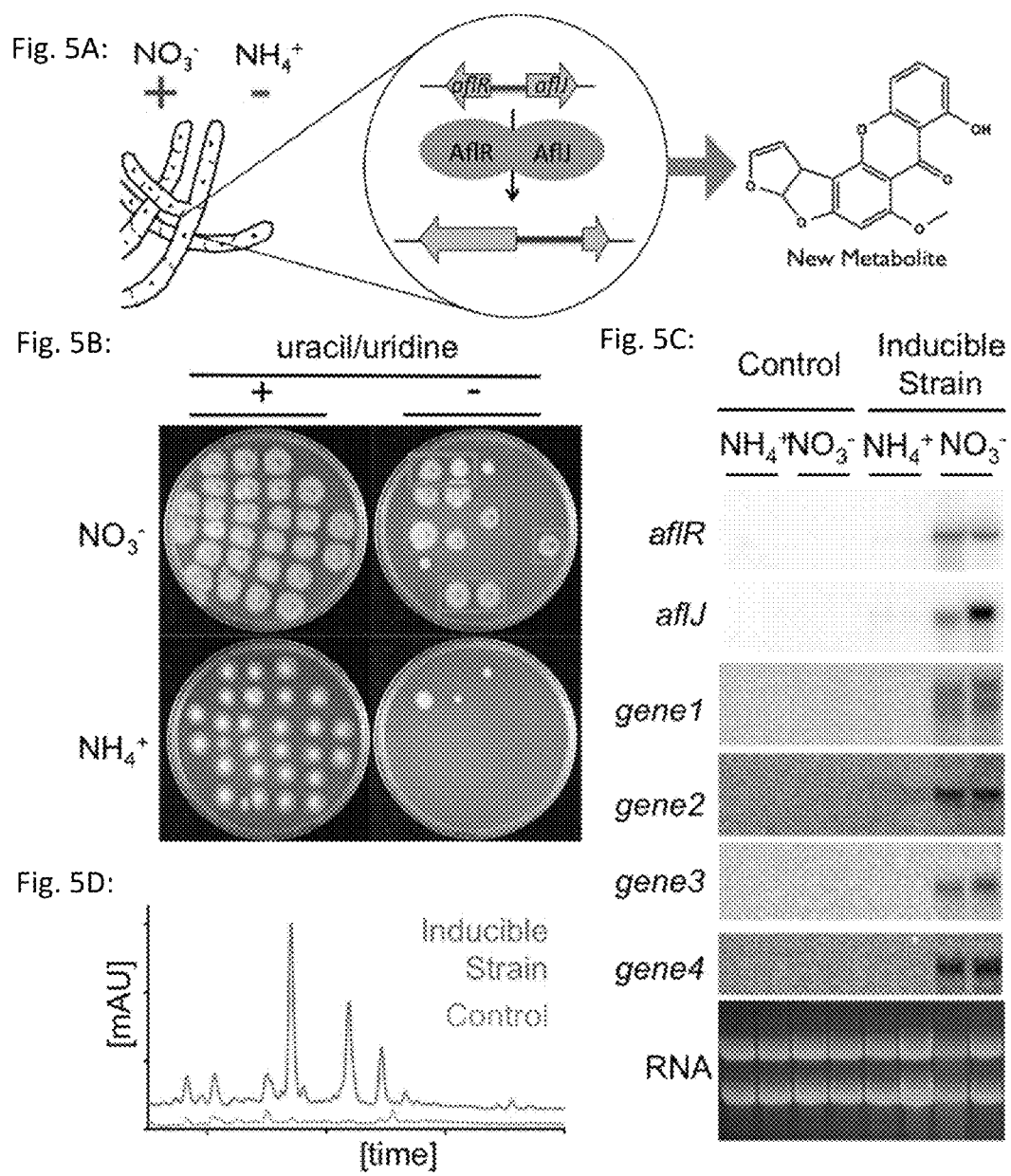

New Metabolite pWhite:
ctctggaacagtctcgccgtcttgctcgtgcatttgaccaagccacttttcaggtggcttttggtccctcatgatttacgaatgattcaagcagga
aatctcttgttgagcgaggagtctctcggcagtgatgacgtctattgtagagcctccatgcagtcggctcgagaatgtaacctaatgaaagac
aaccaattcaacggatacccactacgctgaatagtgctgactggtacgatcgcatttgctcaggtcaagcttagatcaaggatcataatcagt
gctctcaatgaccgatccatcgacgaggcccaatagatagtagatatagcttgtttttcgatatgatggtgacacgtgacgccagctctcttcc
ctttccggaacacatgcaaagaacttgattttgagacctaccgggagcgtcgcaatcaaatctgttgaatttctcttcgactcatgttccttgattc
tcaggttttgttgctatcgggccgatgcataacaaggtcaatctatccgtccagcacattctagaacaatcatcgggaatccgaacgagtgt
tggacccgaaaacagaccgttgcctctttcatcatgacggaagccctgcaaggctgaagcacagttaggattagtggaagagttccacttgg
ttcccaagactgattccgatctagatctttccattcatgaatcgaccaaataggagccttgcgtgatggcccacaaaacagtgagggttgtattc
gaacaacctgattagaacggcttgccgatgctacattgcctacgatccaggaatagcacagagatgtacggagcggactcgaagtatgttg
caaccaggtataggaagtggcccaccctcgcgaaaaggcaaaaaggactgcatcagtataaaagtctgctcatagaagatcgcgcgtatt
ccgccgctgattctgggatgaactcaattgcctgatcagcggacttgactctcctctcctgatcgctagcgagagttattctgtgtctgacgaa
atatgttgtgtatatatatatatgtacgttaaaagttccgtggagttaccagtgattgaccaatgttttatcttctacagttctgcctgtctaccccatt
ctagctgtacctgactacagagtagtttaattgtggttgaccccacagtcggaggcggaggaatacagcaccgatgtggcctgtctccatcc
agattggcacgcaattttacacgcggaaaagatcgagatagagtacgactttaaatttagtccccggcggcttctattttagaatatttgagatt
tgattctcaagcaattgatttggttgggtcaccctcaattggataatatacctcattgctcggctacttcaactcatcaatcaccgtcataccccgc
atataaccctccattcccacgatgtcgtccaagtcgcaattgacttacggtgctcgagccagcaagcaccccaatcctctggcaaagagactt
tttgagattgccgaagcaaagaagacaaacgttaccgtctctgctgatgtgacgacaacccgagtactcctggacctcgctgaccgtacgg
aagctgttggatccaatacatatgccgtctagcaatggactaatcaacttttgatgatacaggtctcggtccctacatcgccgtcatcaagaca
cacatcgacatcctcaccgatttcagcgtcgacactatcaatggcctgaatgtgctggctcaaaagcacaacttttttgatcttcgaggaccgca
aattcatcgacatcggcaataccgtccagaagcaataccacggcggtgctctgaggatctccgaatgggcccacattatcaactgcagcgtt
ctcccctggcgagggcatcgtcgaggctctgcccagacccgcatctgcgcaagacttcccctatggtcctgagagaggactgttggtcctgg
cagagatgacctccaaaggatcgctggctacggcgagtataccaaggcatcggttgactacgctcgcaaatacaagaacttcgttatggg
tttcgtgtcgacgcgggccctgacggaagtgcagtcggatgtgtcttcagcctcggaggatgaagatttcgtggtcttcacgacgggtgtga
accctcttccaaaggagataagcttggacagcaataccagactcctgcatcggctattggacgcggtgccgactttatcatcgccggtcga
ggcatctacgctgctcccgacccggttgaagctgcacagcggtaccagaaagaaggctggaangctatatggccagagtatgcggcaa
gtcatgatttcctcttggagcaaaagtgtagtgccagtacgagtgttgtggaggaaggctgcatacattgtgcctgtcattaaacgatgagctc
gtccgtattggccctgtaatgccatgttttccgccccaatcgtcaaggttttccctttgttagattcctaccagtcatctagcaagtgaggtaa
gctttgccagaaacgccaaggcttatctatgtagtcgataagcaaagtggactgatagctaatatggaaggtccctcaggacaagtcgacc
tgtgcagaagagataacagcttggcatcacgcatcagtgcctcctctcagacagaatgcggccgcatgacgcgaatcactttactatgacaa
agggcgaaaaggcaaaggagcttgctacttttcatgaagaatgcgttgggggtttgtgagcgccggttggtctgataatgtcaattgtttgcttt
ggttttggcttaggttttgatccattaatgctattctattgttgctcataaggttttactttccgtttcatcttgtactctaaacataaagggtaaacaa
taataatcctctggtctaatataaaggttcttgagagactgcatctaagtgttcagccacaatcaattgcgatactctatttcctagctatttaacg
cccaaagttttggaaacccggacaatagtgcgaacaacccaactagtagccgcgggtataaacggtgtcgcataaaaagagcaaatgtaca
ctagcattgcagtcaaaacaaccctgggtcaatgcaatgtcataattcataaagggccgcaatatgatgacatgctgtagtcgtctaagcaag
tgaaggcatgtaaggtagtagtaggcacggtaacatccagtttcagcactccctgtaaacgtcatagagtgtctggcagtggggaaagagg
cccaagaaacccagtccaacgtcaaatctgaacagaaaagatttcagaaggataggacttccgtgagcttccactcagaaaaacccgga
agatgaatggattgctctggtttgtattgatcgattgaagtaaaacttaattgagagaggaggcatatggtatgtaggcgcgacgggttattca
tagggacatctcagaactaaacctaagagcgcttccgcggcctggaaaattagatccgttattattgattccagggcttgtaggacggctgta
gttgttcgcatttaactttgggcttcgtggttgggtgcttgttgagcgtgtggatgggcgattcttgcggatctcgcggagctcgtcctcttcttct
ggaggagatcttcgcgtactgacagcacaggggatacgcaggaaagaacatgtgagcaaaaggccagcaaaaggccagcaaaaggc
caggaaccgtaaaaaggccgcgttgctggcgttttccataggctccgcccccctgacgagcatcacaaaaatcgacgctcaagtcagag
gtggcgaaacccgacaggactataaagataccaggcgtttccccctggaagctccctcgtgcgctctcctgttccgaccctgccgcttaccg
gatacctgtccgcctttctcccttcgggaagcgtggcgctttctcatagctcacgctgtaggtatctcagttcggtgtaggtcgttcgctccaag
ctgggctgtgtgcacgaaccccccgttcagcccgaccgctgcgccttatccggtaactatcgtcttgagtccaacccggtaagacacgactt
atcgccactggcagcagccactggtaacaggattagcagagcgaggtatgtaggcggtgctacagagttcttgaagtggtggcctaactac

Figure 10 ggctacactagaaggacagtatttggtatctgcgctctgctgaagccagttaccttcggaaaaagagttggtagctcttgatccggcaaacaa
accaccgctggtagcggtggttttttgtttgcaagcagcagattacgcgcagaaaaaaggatctcaagaagatcctttgatcttttctacgg
ggtctgacgctcagtggaacgaaaactcacgttaagggattttggtcatgagattatcaaaaaggatcttcacctagatcctttaaattaaaaa
tgaagttttaaatcaatctaaagtatatatgagtaaacttggtctgacagttaccaatgcttaatcagtgaggcacctatctcagcgatctgtctatt
tcgttcatccatagttgcctgactccccgtcgtgtagataactacgatacgggagggcttaccatctggccccagtgctgcaatgataccgcg
agacccacgctcaccggctccagatttatcagcaataaaccagccaggaaggggccgagcgcagaagtggtcctgcaactttatccgc
ctccatccagtctattaattgttgccgggaagctagagtaagtagtcgccagttaatagtttgcgcaacgttgttgccattgctgcaggcatcgt
ggtgtcacgctcgtcgtttggtatggcttcattcagctccggttcccaacgatcaaggcgagttacatgatcccccatgttgtgcaaaaaagcg
gttagctccttcggtcctccgatcgttgtcagaagtaagttggccgcagtgttatcactcatggttatggcagcactgcataattctcttactgtca
tgccatccgtaagatgcttttctgtgactggtgagtactcaaccaagtcattctgagaatagtgtatgcggcgaccgagttgctcttgcccggc
gtcaacacgggataataccgcgccacatagcagaactttaaaagtgctcatcattggaaaacgttcttcggggcgaaaactctcaaggatctt
accgctgttgagatccagttcgatgtaacccactcgtgcacccaactgatcttcagcatcttttactttcaccagcgtttctgggtgagcaaaaa
caggaaggcaaaatgccgcaaaaaagggaataagggcgacacggaaatgttgaatactcatactcttcctttttcaatattattgaagcattta
tcagggttattgtctcatgagccattatacgaagttatgcaccacgctttcaattcaattcatcattttttttttattctttttttttgatttcggtttccttga
aatttttttgattcggtaatctccgaacagaaggaagaacgaaggaaggagcacagactagattggtatatatacgcatatgtagtgttgaag
aaacatgaaattgcccagtattcttaaccccaactgcacagaacaaaaacctgcaggaaacgaagataaaatcatgtcgaaagctacatataag
gaacgtgctgctactcatcctagtcctgttgctgccaagctatttaatatcatgcacgaaaagcaaacaaactgtgtgcttcattggatgttcgt
accaccaaggaattactggagttagttgaagcattaggtcccaaaatttgttactaaaaacacatgtggatatcttgactgatttttccatggag
ggcacagttaagccgctaaaggcattatccgccaagtacaatttttactcttcgaagacagaaaatttgctgacattggtaatacagtcaaatt
gcagtactctgcgggtgtatacagaatagcagaatgggcagacattacgaatgcacacggtgtggtgggcccaggttattgttagcggtttga
agcaggcggcagaagaagtaacaaaggaacctagaggcctttgatgttagcagaattgtcatgcaaggcctccctatctactggagaatat
actaagggtactgttgacattgcgaagagcgacaaagattttgttatcggctttattgctcaaagagacatgggtggaagagatgaaggttac
gattggttgattatgacaccggtgtgggtttagatgacaagggagacgcattgggtcaacagtatagaaccgtggatgatgtggtctctaca
ggatctgacattatattgttggaagaggactatttgcaaagggaagggatgctaaggtagagggtgaacgttacagaaaagcaggctggg
aagcatatttgagaagatgcggccagcaaaactaaaaaactgtattataagtaaatgcatgtatactaaactcacaaattagagcttcaattttaa
ttatatcagttattacccataacttcgtatagcatacattatacgaagttatcccgggtaccgagctcgaattcgtaacttacacgcgcctcgtatc
ttttaatgatggaataatttgggaatttactctgtgtttatttattttttatgttttgtatttggatttagaaagtaaataaagaaggtagaagagttacg
gaatgaagaaaaaaaataaacaaaggtttaaaaaattcaacaaaaagcgtactttacatatatatttattagacaagaaaagcagattaaata
gatatacattcgattaacgataagtaaaatgtaaaatcacaggattttcgtgtgtggtcttctacacagacaagatgaaacaattcggcattaata
cctgagagcaggaagagcaagataaaaggtagtatttgttggcgatcccctagagtcttttacatcttcggaaaacaaaaactatttttctttta
atttcttttttactttctattttaattatatatttatattaaaaaatttaaattataattattttatagcacgtgatgaattcgtaatcatggtcatagctgt
ttcctgtgt

Figure 10 continued pYellow:
gatggagattggcgccgtctttatctgttgtgccaccagtctctttaaacatcagaaacgtcgggccagatgtagaatcggccacggacctg
acaattctcgacgtctctgagatccccgacaagttctcagtggagcgaatgaaggattcaacgaagcccacacccgctttctcgaggttctc
cgcctagctggtgggttgaaccgcttactcagtgtcgaaaggataaatgagatcaattctcccgtgaagccattcagcaaggtatccatgcg
gctctcgtggaacacaatgctaacgccctcaccaccctccttaagctcgacgagtttaccttccgttgccagaacaaccttgtagatgccgtgt
ataccctaccaccagagcatttccgcaccgctgtccgtgtggcacgacacgactctagcttcttccagctctgctgcgtgcgagtgctgagt
ctgttccctacgacgattcggagatcacgcactgggcagtactacgggtggtccttttgaacaatggctactggatttcatgctgcagctgcc
ggagcaaatcagggcgacaaccaagggaagtcaacaaatgttctatcatggggggcttaatacagcaagtgccatgacagaaaggtatctt
cgagatattctgggaacggatgagcttaaggtctggctagaagagtcgtcgtacgattttcccagcgaatggattgttgagagttgatgttgaa
gatattgaacaaatttctgtggtgatgagcgctggaagaatcagtgtacaacgaaaggagcagacaagactcccttgctatactcaggtgtg
acacctgcaaatccagtaggaaaatacggtaattaatcccaggggtcttttccctccgccaggcaccacgcccttgccggaaacgtcgcgc
agtcgcgttcagcaccaggtacattccaatcaacaatgcaagaatgtgaaacgcgaagtatatatcagcgaacaacatcaagccgacaggc
gcgccgcggactgagttatggatgactcccttcgatgatacccttagcagaagtgttcttaaattgcgggaagaggccgttcaggagtctg
gctcgtttgatcacatgggattaaaatatggtgttgaggctgggatattttatgttttgtctcttgcgcttcgatatcaacagattgacaataatgaa
taactatctacggactatgaatgcagctcgatctactccgtatttagtcgggcaatctcccgtagaagatgctagactgcgctgaaagactagg
cacagttaattgccgcggatcacgtcaggcctgacaaatgacaggtggaccttcatgtaatcgcacgatgagtcagcgcctcttctccccg
ccgacttgcagctgcggatgtcccgaggagccgaacattgaatctatcccaagagtgactgaaatatgattgcaatcgtcgtcttttcttgca
gagaatgtggtgaggtgatcaatcgtgttttctttcatatattatattctgtaatgatcatactttgttgagataccgtctctaaaattgtactttcgc
ctccctcctccctctcaagtccgtcatcgcaatgtcgaatttaccgtccatgcttctccgtcttttggggcgcaaacgcctaccacgccgcag
cccgtcgacgagctttctctcaagtcgaacatcacatcagccctgcgttacactccagattagcgaactccgagatgagacttccagcca
gatcagcagcatagacactgaccgcgggacatgacccctgcggttcccgcatcattactctccccatcctcactcctccagcaacccccg
ggggctcgatcaataccgcggagctgcttcaacgacccaattagctggcgcacggcaagggtcaacacatactaagcccccgaggttg
ctttctcgtcttcccaatgtcgaatgtatcgtccgcgctcggatacccacgacaactggcgcggagatgtttcttcacctgtaccacaatgactt
agacaacaaagagcatttggcgattgtgtttggaaatacaattcgaagcagaagcttggacaagatccggcctggagagacggagatggat
cgcatgatccgtggcgcgtatgtcgggaaactccgaccgggccgtgtgagcagctggtatgacgagagagaagctgaagaggccgcca
gtccggaagctggcgcgcgctgtatccagtccgcacacactgccgcgaagtagcctcaaggaggcacctcttgtgagaatccattcggagt
gctacactggtgagacggcttggtctgcacgctgcgactgcggcgagcagctcgatgaagcagctcgcctcatgtcgctgcctatggaaa
cgttggcagaggctgcgtcaccgccggatggggcggtaccgtcaaatgctgctggaggtgtaattgtgtaccgtcgccaagaaggacga
ggcattgggctgggcgagaaactgaaagcgtacaatcttcaggatctgggatcagacacgtggaagccaatctcctgcttcgccaccctg
cggatgcaagaagttatggattagctacggcgatcctggtggatcttggtctagggattgactcgaatccgcacggcatccgactactcacg
aataacccggacaagattcgagcggttgagggacccaaccgagaagtggtggtgaaagagcgggtgccgatggtgccattggcatgga
gatcgggtggaaagatgggaatcaagagttccgaggtcgaagggtatctgagaacgaaggtatgtcgacaatctatctcttgcaagctagct
tattttctcatcattcttaaacaatgtctcactctctcctcgcagatatcgaaatgggccattgctccaatgaacctatcccttcggttagtaac
cttgtgctggaagtacgccttcctgcttttggacttagccaagtcgacacggtgtatgctcgtcacactcatgtaacggttctgcagcgcaaac
gttctggtcacgttattcgctttgtccatttgtcttttttgtgcggtacataaactagaggattagcgcactttgtacatgatgttcccgacatgtca
cattaggcctcgattggtcaaaataatccctctctaacctctggttcgcatactcttaaatgcagctcagtctctagacggactagttcctcctgc
agtggatgtctgacgagtgtctgcaaggaccgtttccgtgtccagttagttccaatcacccggatatcggcgagacgtcggccgattgagat
cactgagtcaatggcgttgagtggccacttgttggacgggggttgatgtttgggattcttaggtgagctctcatattcgtacttacaagatgtttgttc
taaaattatttaataattattttttaatctctatgaaatggagaagcttttttttctctcttttttggctctttaaattatatcagcatattttattaaatcattg
gaactctagatgtacgccccagagaagtagaactacatattcccaatcaacctcagaatacctctgaccctcccagccagcgtgatctgatac
ccgtctcaacaaccccttgcacatctcaaatgcaccatccccattctcttctccgcttctccttcataatcggataatccacgcgcggcgg
aatcctcgtcgccataaggcgcgggaacctgtcaacgcaaatcgctttgatattacttacgccccgcagaccttcttcgcccgcaaaccggc

Figure 11

```
cataccccagatcccttgacgccgccgaatggcagctgtactgtgtagtagctgccaaaatcgttaacagagaccatgcctgcctttattcctg
agacacaagcattcacgtcgcgcgtgttgtagccaaataccgaggcacctagcgcgtattgggtagaatttgcgatggtgattgcgtcggag
acggaagatgcacgcatcatgaggaagacggggcgaagagctctgtttgggcaatttccatggagggcgtgacgtctgcaaggagggt
cggtgtgaaatagtgaccgagcggataggttgggtgttcgaattgttcccaccagcgacgaggcgagcaccttggctgacggcgcgctg
aatgagaaactccaagcgggagaaagaggccggggagatcatggcccccacgtctggggcacctgacttgttgtttgggttgttgggcttt
gtgtctagtaagactgaaccgaggcggagggctttaatgcgggaggtgacggtgtcaaggagtttgtcgtatacgccagggagggcaatg
acgcgctcaacgccgatagctcgaattcactggccgtcgttttacaacgtcgtgactgggaaaaccctggcgttacccaacttaatcgccttg
cagcacatccccctttcgccagctggcgtaatagcgaagaggcccgcaccgatcgcccttcccaacagttgcgcagcctgaatggcgaat
ggcgcctgatgcggtatttctccttacgcatctgtgcggtatttcacaccgcatatatcggatcgtacttgttacccatcattgaatttgaacatc
cgaacctgggagttttcccctgaaacagatagtatatttgaacctgtataataatatatagtctagcgcttacggaagacaatgtatgtatttcggt
tcctggagaaactattgcatctattgcataggtaatcttgcacgtcgcatcccggttcattttctgcgtttccatcttgcacttcaatagcatatctt
tgttaacgaagcatctgtgcttcattttgtagaacaaaaatgcaacgcgagagcgctaattttcaaacaaagaatctgagctgcattttacaga
acagaaatgcaacgcgaaagcgctatttaccaacgaagaatctgtgcttcattttgtaaaacaaaaatgcaacgcgagagcgctaattttc
aaacaaagaatctgagctgcattttacagaacagaaatgcaacgcgagagcgctatttaccaacaaagaatctatacttcttttttgttctaca
aaaatgcatcccgagagcgctattttctaacaaagcatcttagattacttttttctccttgtgcgctctataatgcagtctcttgataacttttgca
ctgtaggtccgttaaggttagaagaaggctactttggtgtctattttctcttccataaaaaagcctgactccactccgcgtttactgattacta
gcgaagctgcgggtgcattttttcaagataaaggcatccccgattatatctataccgatgtggattgcgcatacttgtgaacagaaagtgata
gcgttgatgattcttcattggtcagaaaattatgaacggttcttctattttgtctctatatactacgtataggaaatgtttacattttcgtattgtttcg
attcactctatgaatagttcttactacaattttttgtctaaagagtaatactagagataaacataaaaatgtagaggtcgagtttagatgcaagtt
caaggagcgaaaggtggatgggtaggttatataggatatagcacagagatatatagcaaagagatactttgagcaatgtttgtggaagcg
gtattcgcaatatttagtagctcgttacagtccggtgcgttttggtttttgaaagtgcgtcttcagagcgcttttggttttcaaaagcgctctgaa
gttcctatacttctagctagagaataggaacttcggaataggaacttcaaagcgtttccgaaaacgagcgcttccgaaaatgcaacgcgagc
tgcgcacatacagctcactgttcacgtcgcacctatatctgcgtgttgcctgtatatatatatacatgagaagaacggcatagtgcgtgtttatgc
ttaaatgcgtacttatatgcgtctatttatgtaggatgaaaggtagtctagtacctcctgtgatattatcccattccatgcggggtatcgtatgcttc
cttcagcactaccctttagctgttctatatgctgccactcctcaattggattagtctcatccttcaatgctatcatttccttgatattggatcgatccg
atgataagctgtcaaacatgagaattgggtaataactgatataattaaattgaagctctaatttgtgagtttagtatacatgcatttacttataatac
agttttttagtttgctggccgcatcttctcaaatatgcttcccagcctgcttttctgtaacgttcaccctctaccttagcatcccttcccttttgcaaat
agtcctcttccaacaataataatgtcagatcctgtagagaccacatcatccacggttctatactgttgacccaatgcgtctccctgtcatctaaa
cccacaccgggtgtcataatcaaccaatcgtaaccttcatctcttccacccatgtctctttgagcaataaagccgataacaaaatctttgtcgctc
ttcgcaatgtcaacagtaccettagtatattctccagtagatagggagcccttgcatgacaattctgctaacatcaaaaggcctctaggttcctt
gttactcttctcgccgcctgcttcaaaccgctaacaatacctgggcccaccacaccgtgtgcattcgtaatgtctgcccattctgctatctgtata
cacccgcagagtactgcaattgactgtattaccaatgtcagcaaatttctgtcttcgaagagtaaaaaattgtacttggcggataatgcctta
gcggcttaactgtgccctccatggaaaaatcagtcaagatatccacatgtgtttttagtaaacaaattttgggacctaatgcttcaactaactcca
gtaattccttggtggtacgaacatccaatgaagcacacaagtttgttgctttcgtgcatgatattaaatagcttggcagcaacaggactagga
tgagtagcagcacgttcctatatgtagctttcgacatgatttatcttcgttcctgcatgttttgttctgtgcagttgggtaagaatactgggcaa
tttcatgtttcttcaacactacaaatgcgtatatataccaatctcatgttcttcaacactacaaatgcgtatatataccaatctaagtctgtgctcctt
ccttcgttcttccttctgttcggagattaccgaatcaaaaaatttcaaagaaaccgaaatcaaaaaaaagaataaaaaaaaatgatgaattg
aattgaaaagctaattcttgaagacgaaaggggcctcgtgatacgcctatttttataggttaatgtcatgataataatggttcttagacgtcaggtg
gcactttcggggaaatgtgcgcggaaccccctatttgtttatttttctaaatacattcaaatatgtatccgctcatgagacaataaccctgataaat
gcttcaataatattgaaaaaggaagagtatgagtattcaacatttccgtgtcgcccttattccctttttgcggcattttgccttcctgtttttgctcac
ccagaaacgctggtgaaagtaaaagatgctgaagatcagttgggtgcacgagtgggttacatcgaactggatctcaacagcggtaagatcc
ttgagagttttcgccccgaagaacgttttccaatgatgagcacttttaaagttctgctatgtggcgcggtattatcccgtattgacgccgggcaa
gagcaactcggtcgccgcatacactattctcagaatgacttggttgagtactcaccagtcacagaaaagcatcttacggatggcatgacagta
agagaattatgcagtgctgccataaccatgagtgataacactgcggccaacttactctgacaacgatcggaggaccgaaggagctaaccg
cttttttgcacaacatgggggatcatgtaactcgccttgatcgttgggaaccggagctgaatgaagccataccaaacgacgagcgtgacacc
```

Figure 11 continued acgatgcctgtagcaatggcaacaacgttgcgcaaactattaactggcgaactacttactctagcttcccggcaacaattaatagactggatg
gaggcggataaagttgcaggaccacttctgcgctcggcccttccggctggctggtttattgctgataaatctggagccggtgagcgtgggtc
tcgcggtatcattgcagcactggggccagatggtaagccctcccgtatcgtagttatctacacgacggggagtcaggcaactatggatgaa
cgaaatagacagatcgctgagataggtgcctcactgattaagcattggtaactgtcagaccaagtttactcatatatactttagattgatttaaaa
cttcatttttaatttaaaaggatctaggtgaagatcctttttgataatctcatgaccaaaatcccttaacgtgagtttcgttccactgagcgtcaga
ccccgtagaaaagatcaaaggatcttcttgagatcctttttttctgcgcgtaatctgctgcttgcaaacaaaaaaaccaccgctaccagcggtg
gtttgtttgccggatcaagagctaccaactctttttccgaaggtaactggcttcagcagagcgcagataccaaatactgtccttctagtgtagcc
gtagttaggccaccacttcaagaactctgtagcaccgcctacatacctcgctctgctaatcctgttaccagtggctgctgccagtggcgataa
gtcgtgtcttaccgggttggactcaagacgatagttaccggataaggcgcagcggtcgggctgaacggggggttcgtgcacacagcccag
cttggagcgaacgacctacaccgaactgagatacctacagcgtgagctatgagaaagcgccacgcttcccgaagggagaaaggcggac
aggtatccggtaagcggcagggtcggaacaggagagcgcacgagggagcttccagggggaaacgcctggtatctttatagtcctgtcgg
gtttcgccacctctgacttgagcgtcgatttttgtgatgctcgtcaggggggcggagcctatggaaaaacgccagcaacgcggcctttttacg
gttcctggccttttgctggccttttgctcacatgttctttcctgcgttatcccctgattctgtggataaccgtattaccgcctttgagtgagctgatac
cgctcgccgcagccgaacgaccgagcgcagcgagtcagtgagcgaggaagcggaagagcgcccaatacgcaaaccgcctctccccg
cgcgttggccgattcattaatgcagctggcacgacaggtttcccgactggaaagcgggcagtgagcgcaacgcaattaatgtgagttagct
cactcattaggcaccccaggctttacactttatgcttccggctcgtatgttgtgtggaattgtgagcggataacaatttcacacaggaaacagct
atgaccatgattacgccaagcttgcatgcctgcaggtcgactctagaggatccccctggcacgacaggtttcccgactggaaagcgggca
gtgagcgcaacgcaattaatgtgagttagctcactcattaggcaccccaggctttacactttatgcttccggctcgtatgttgtgtggaattgtga
gcggataacaatttcacacaggaaacagctatgaccatgattacgccaagctcgaaattaaccctcactaaagggaacaaaagctggagct

Figure 11 continued

Promoter stcA / B Sequence tggactcgcaatcagagggggacaatctgcatcatgaattcccttctgttggaacgcctgatatagtacgcttgtgcggttgacccagtgta
tcgggcactcaaccggtcatctattcttgactcggtgaagagagactgcaatcggcagatgctcgggtatcgctaaagaatactctgtcctctt
cccagtaaacccggtacagtcagcgacggatcacggtcagcgaggccatgaccgactcggcagctccttgattgacaccttgcacatgt
aagataaaataggcaatctgaatctcaccgttagcttagaatcatggaactgcagaccatactattttcgcaataaacggctccagg

Figure 12

Promoter stcI Sequence actgaggactcagggggggtagctaagtgggctgcagacggatcagatacaataacgccatacgttatggtggacatttaccagacggatg
aagatccaattaagaacattgtagctcggtgaccgacattcaacataagacaaatcgaacctcgcgatgaaagtccgtagcagacaacaga
tcgcttcaaca

Figure 13

Promoter AN11017 / stcN Sequence

Ggttttgaagagttccaggagtatgaacttatgcttggggtatctgccaggtctctttttctcgtcttataccgacgcctacatgggtctcggcaa
gcgatcggtgagggctccgccatgtgccgaagtattggtacgtggtggccggtttattaacttcgcgagagcctaagctacagacgagcac
catcagacagaccatcgtcact

Figure 14

Promoter stcQ Sequence ggctactgcatgccattctattctggatcacaatgtgccaatatttgtgatgtaatactagccccgaaccccgaagcacggtgaggctcgctga
gcgaagccaaaatcttacattaagtccagatcttggtggtgcaaataccctcacagaaccaaaca

Figure 15

Promoter stcV / W Sequence aitgttcttgctgagtacagatatgatgctgttgagcagttgttgaaccgtcaagacacgcacttatagccatggaccccgctctgccaacctgt
catgcaatgctcggcatgcgattaaccgactcgctggccgaaccctgactataatgtgtccattatatgaacattgggatatctaaaggcgatt
catatccgttttagaccatacagcacacaatacccccgca

Figure 16

METHODS AND SYSTEMS FOR PRODUCING FUNGAL SECONDARY METABOLITES

CROSS REFERENCE TO RELATED APPLICATIONS

This application claims the benefit of U.S. Provisional Patent Application Ser. No. 62/116,730, filed Feb. 16, 2015, which is incorporated by reference herein as if set forth in its entirety.

STATEMENT REGARDING FEDERALLY SPONSORED RESEARCH/DEVELOPMENT

This invention was made with government support under A1065728 awarded by the National Institutes of Health and 1136903 awarded by the National Science Foundation. The government has certain rights in the invention.

BACKGROUND

Natural products or secondary metabolites (SMs) have been invaluable as platforms for developing front-line drugs. Between 1981 and 2006, 5% of the 1031 new chemical entities approved as drugs by the FDA were natural products and for application in cancer another 47% were natural-product-derived. In addition, SMs are major sources of innovative therapeutic agents for both bacterial and fungal infectious diseases, cancer, lipid disorders, and immunomodulation. Fungal SMs have proven to be a particularly important source of new leads with useful pharmaceutical activities. A recent literature survey of fungal metabolites, covering 1500 fungal SMs that were isolated and characterized between 1993 and 2001, showed that more than half of the molecules had antibacterial, antifungal or antitumor activity.

However, the majority of existing fungal species has not been characterized for their metabolic potential. One major roadblock in this endeavor is that some species are not culturable under laboratory conditions and/or their secondary metabolite gene clusters are silent creating manufacturing difficulties as SMs are usually complicated chemically making production via traditional synthetic routes impossible.

Previous strategies on activating fungal SMs have focused mainly on 1) activating endogenous gene clusters by either over-expressing the pathway-specific transcription factor or manipulating global regulators and 2) expressing the entire gene cluster in a heterologous host. Although successful in some cases, these strategies have significant disadvantages. As not all fungal species are amenable to genetic manipulation, strategies that focus on endogenous activation are impossible in these species. If genetic manipulations are possible, activation of an otherwise silent cluster still depends the presence of a cluster-specific transcription factor. However, not all SM clusters contain transcription factors. Another major disadvantage of overexpressing SMs is that many SMs are toxic to the host fungus, thereby making the isolation of significant amounts of the desired compound difficult.

Approaches expressing fungal gene clusters in heterologous hosts (mainly *Saccharomyces cerevisiae* or *Aspergillus* spp.) focused on amplification of the entire gene cluster including native promoters. Although these approaches led to expression of the targeted gene clusters in some cases, the use of native promoters cannot guarantee controlled activation of the genes. As a result, those clusters still remain silent in the new host in most cases. Exchange of native promoters with constitutively expressing promoters for an entire gene cluster is unfeasible up to now. Although a few constitutively promoters for fungal species are commonly used, not enough promoters are known in order to fuse all cluster genes to unique promoters. The use of the same promoter sequence for several genes of a cluster is impossible due to the yeast cloning technique applied for assembling the gene cluster in a suitable plasmid. Cloning of gene clusters is achieved by PCR-based amplification of the desired DNA region and subsequent yeast recombination-based cloning. In general, the gene cluster is amplified in several 1-2 kb pieces by use of primers with short overlapping 5'-overhangs. These fragments are co-transformed with a linearized shuttle vector into yeast cells for assembly by its recombination machinery. The yeast recombination-based system requires unique promoters be used for each gene to be expressed in the plasmid. The use of the same promoter sequences would result in incorrect assembly of the desired plasmid.

Needed in the art are improved methods and systems for producing fungal secondary metabolites.

SUMMARY OF THE INVENTION

In one aspect, the present invention is a genetically modified *Aspergillus nidulans* for producing one or more secondary metabolites comprising an *Aspergillus nidulans* organism comprising an engineered gene cluster comprising the *Aspergillus nidulans* sterigmatocystin gene cluster transcriptional enhancer genes aflR and aflJ operably linked to a nitrate-inducible promoter, wherein none of the other genes included in the wild type *A. nidulans* sterigmatocystin gene cluster are present in the engineered gene cluster; wherein the genetically modified *Aspergillus nidulans* is capable of nitrate-induced expression of the aflR and aflJ gene products.

In one embodiment, the wild type *A. nidulans* sterigmatocystin gene cluster is not present, and the engineered gene cluster is inserted where the wild type *A. nidulans* sterigmatocystin gene cluster normally occurs.

In one embodiment, the nitrate-inducible promoter is niiA/niaD.

In one embodiment, the genetically modified *A. nidulans* further comprises an exogenous expression vector comprising one or more *A. nidulans* sterigmatocystin gene cluster promoters operably linked to one or more protein-encoding genes, and the one or more *A. nidulans* sterigmatocystin gene cluster promoters are inducible by AflR/AflJ.

In one embodiment, the genetically modified *A. nidulans* is strain TPMW2.3.

In one embodiment, the nitrate-inducible promoter is repressible by ammonium.

In one embodiment, the one or more protein-encoding genes are from a fungal secondary metabolite gene cluster, and the genetically modified *A. nidulans* is capable of nitrate-induced expression of the secondary metabolite.

In one embodiment, the exogenous expression vector comprises a fungal secondary metabolite gene cluster.

In one embodiment, the proteins encoded by the protein-encoding genes are biosynthetic enzymes.

In one aspect, the present invention discloses an expression vector for producing fungal secondary metabolites. The expression vector comprises one or more *A. nidulans* sterigmatocystin gene cluster promoters operably linked to one or more protein-encoding genes that are not part of the *A.* nidulans sterigmatocystin gene cluster, and the one or more *A. nidulans* sterigmatocystin gene cluster promoters are inducible by AflR/AflJ.

In one embodiment, the expression vector comprises a fungal gene cluster other than the *A. nidulans* sterigmatocystin gene cluster.

In one embodiment, the fungal gene cluster is a secondary metabolite gene cluster.

In one aspect, the present invention discloses a kit for producing fungal secondary metabolites. The kit comprises any of the genetically modified *A. nidulans* as discussed above; and any of the expression vector as discussed above.

In one aspect, the present invention discloses a method for producing fungal secondary metabolites (SM). The method comprises contacting the genetically modified *A. nidulans* as discussed above with nitrate, whereby one or more of the proteins encoded by the expression vector are expressed, and whereby a fungal secondary metabolite is produced.

In one embodiment, the method further comprises the step of producing the genetically modified *A. nidulans* as discussed above by transforming the genetically modified *A. nidulans* of as discussed above with the expression vector as discussed above.

In one embodiment, the strain of *A. nidulans* is *A. nidulans* strain TPMW2.3.

DESCRIPTION OF DRAWINGS

The patent or application file contains at least one drawing executed in color. Copies of this patent or patent application publication with color drawing(s) will be provided by the Office upon request and payment of the necessary fee.

FIG. 5A is a diagram showing schematic overview of the technology. Nitrate inducible AflR AflJ transcription factors induce gene expression of SM cluster genes fused to ST promoters, thereby leading to the production of a new metabolite. FIG. 5B shows growth of *A. nidulans* strains harboring the aflR/aflJ nitrate inducible construct expressing pyrG under control of each of the 26 ST promoters grown on indicated media. Strains expressing pyrG when induced by nitrate, thereby allowing growth without uracil/uridine, are boxed in green. FIG. 5C shows induction of aflR, aflJ, and four genes from *A. terreus* expression by nitrate analyzed by northern blot analysis. FIG. 5D is a graph showing HPLC analysis of the *A. nidulans* strain expressing the new cluster genes on inducing nitrate conditions showing appearance of a novel peak.

FIG. 6A: Coding regions from a fungal gene cluster of choice will be amplified by PCR and fused to inducible stc promoters and assembled into the plasmids pYellow and pWhite by yeast recombinational cloning, respectively. Plasmids pYellow and pWhite harbor selection markers for uracil/uridine and riboflavin prototrophy between flanking DNA regions of genes responsible for changing spore colors of positive transformants to yellow and white, respectively. FIG. 6B: The two constructs can be transformed into the *A. nidulans* strain TPMW2.3 harboring the nitrate inducible aflR/aflJ construct thereby allowing for production of new secondary metabolites.

FIG. 8A: Northern blot expression analysis of aflR and the ST gene stcU in the *A. nidulans* WT and a strain harboring the mutated $aflR^{S323A,S381A,S382A}$ allele ($aflR^{MUT}$). R=repressing conditions, I=inducing conditions. FIG. 8B: ST production visualized by thin layer chromatography in the *A. nidulans* WT and a strain harboring the mutated $aflR^{S323A,S381A,S382A}$ allele ($aflR^{MUT}$). R=repressing conditions, I=inducing conditions.

FIG. 9A: Photographs of the white spore producing control strain TPMW8.2 and TJSF1.1 that expresses the *F. fujikuroi* carRA and carB gene under aflA and aflB promoters. TJSF1.1 displays an orange color due to ß-carotene production. FIG. 9B: Northern blot gene expression studies of TPMW8.2 and TJSF1.1 under inducible and repressible conditions showing gene expression for aflR and carB. FIG. 9C: HPLC analysis of TPMW8.2 and TJSF1.1 under inducible nitrate conditions compared to a ß-carotene standard. TJSF1.1 shows production of ß-carotene production and additional intermediates.

FIG. 10 shows DNA sequence of pWhite (SEQ ID NO:1).

FIG. 11 shows DNA sequence of pYellow (SEQ ID NO:2).

FIG. 12 shows DNA sequence of promoter stcA/B (SEQ ID NO:3).

FIG. 13 shows DNA sequence of promoter stcI (SEQ ID NO:4).

FIG. 14 shows DNA sequence of promoter AN11017/stcN (SEQ ID NO:5).

FIG. 15 shows DNA sequence of promoter stcQ (SEQ ID NO:6).

FIG. 16 shows DNA sequence of promoter stcV/W (SEQ ID NO:7).

DESCRIPTION OF THE INVENTION

I. In General

Figure 1:
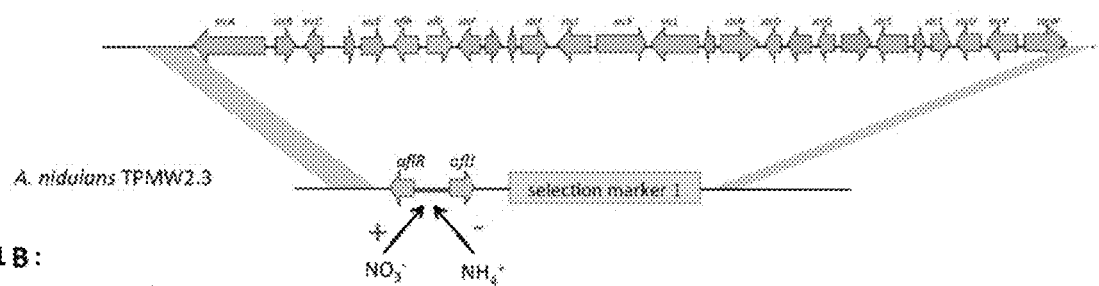
FIGS. 1A and 1B are diagrams and graphs showing the structure and construct of Inducible aflR/aflJ *Aspergillus nidulans* strain. The *A. nidulans* strain TPMW2.3 is derived from *A. nidulans* WT. The *A. nidulans* strain TPMW2.3 contains an $NO_3^-$-inducible aflR/aflJ construct. Specifically, the *A. nidulans* strain TPMW2.3 is derived from LO8030 (pyrG-, pyroA-, riboA-=three selection markers). ST cluster is deleted. niiA/niaD promoter (that drives expression of aflR/aflJ) is integrated in ST cluster region using selection marker 1 (pyroA). The strain has green spores and riboflavin and uracil, uridine auxotrophy.
Figure 1:
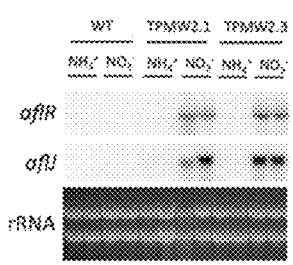
Figure 2A:
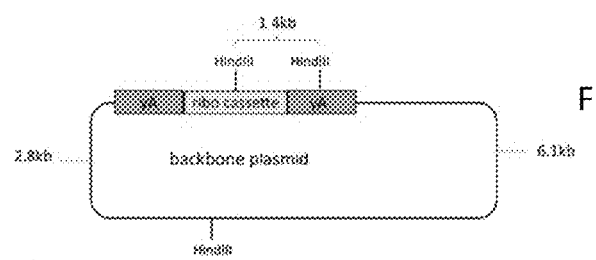
FIGS. 2A, 2B and 2C are diagrams and graphs showing construction of test plasmids according one embodiment of the present invention.
Figure 2B:
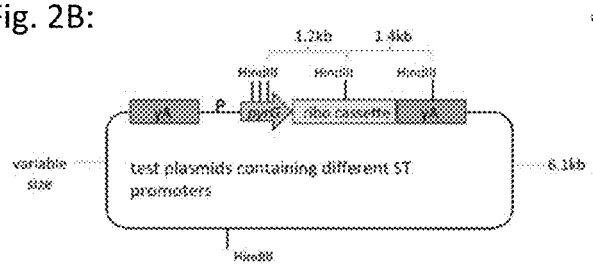
Figure 2C:
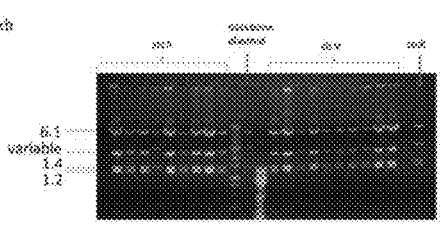

Before the present polypeptides, nucleic acids, and methods are described, it is understood that this invention is not limited to the particular methodology, protocols, cell lines, vectors, and reagents described, as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. Thus, for example, reference to "a cell" includes a plurality of such cells, reference to the "vector" is a reference to one or more vectors and equivalents thereof known to those skilled in the art, and so forth.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications mentioned herein are incorporated herein by reference for the purpose of describing and disclosing the polypeptides, polynucleotides, cell lines, vectors, and methodologies which are reported in the publications which might be used in connection with the invention. Nothing herein is to be construed as an admission that the invention is not entitled to antedate such disclosure by virtue of prior invention.

The practice of the present invention will employ, unless otherwise indicated, conventional techniques of molecular biology, microbiology, recombinant DNA, and immunology, which are within the skill of the art. Such techniques are explained fully in the literature. See, for example, Molecular Cloning A Laboratory Manual, 2nd Ed., ed. by Sambrook. Fritsch and Maniatis (Cold Spring Harbor Laboratory Press: 1989); DNA Cloning. Volumes I and II (D. N. Glover ed., 1985); Oligonucleotide Synthesis (M. J. Gait ed., 1984); Mullis et al. U.S. Pat. No. 4,683,195; Nucleic Acid Hybridization (B. D. Hames & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Calos eds., 1987, Cold Spring Harbor Laboratory); Methods In Enzymology, Vols. 154 and 155 (Wu et al. eds.), Immunochemical Methods In Cell And Molecular Biology (Mayer and Walker, eds., Academic Press, London, 1987); Handbook Of Experimental Immunology, Volumes I-IV (D. M. Weir and C. C. Blackwell, eds., 1986); Cell Culture and Somatic Cell Genetics of Plants. Vol. 1 (I. K. Vasil, ed. 1984); R. V. Stanier, J. L. Ingraham, M. L. Wheelis, and P. R. Painter, The Microbial World, (1986) 5th Ed. Prentice-Hall.

II. Definitions

The term "secondary metabolites" or "SMs," as used herein, refers to organic compounds that are not directly involved in the normal growth, development, or reproduction of an organism. Unlike primary metabolites, absence of secondary metabolites does not result in immediate death, but rather in long-term impairment of the organism's survivability, fecundity, or aesthetics, or perhaps in no significant change at all. Secondary metabolites are often restricted to a narrow set of species within a phylogenetic group. Secondary metabolites often play an important role in plant defense against herbivory and other interspecies defenses. Humans use secondary metabolites as medicines, flavorings, and recreational drugs.

The term "sterigmatocystin" or "ST," as used herein, refers to a mycotoxin, a carcinogen produced by the fungal genus *Aspergillus*. It appears on crusts of cheese with mold. Sterigmatocystin is also called (3aR,12cS)-8-hydroxy-6-methoxy-3a,12c-dihydro-7H-furo[3',2':4,5]furo[2,3-c]xanthen-7-one. Sterigmatocystin is a toxic metabolite structurally closely related to the aflatoxins (compare general fact sheet number 2), and consists of a xanthone nucleus attached to a bifuran structure. Sterigmatocystin is mainly produced by the fungi *A. nidulans* and *A. versicolor*.

The biosynthetic genes necessary for sterigmatocystin (ST) production in *A. nidulans* are clustered on a ca. 60-kb region on chromosome IV (Brown et al., 1996). The expression of these cluster genes (called stc genes) is regulated by two genes in the cluster, aflR and aflJ. aflR encodes a zinc binuclear cluster DNA binding protein which binds to AflR sites in stc promoters (Fernandes et al., 1998). aflJ, also called aflS (Yu, *Toxins* 2012, 4(11), 1024-1057), encodes a NMR-like protein that interacts with AflR on protein level thereby tuning its transcriptional activity (Chang, 2003). aflR is also regulated by the global regulator of secondary metabolism LaeA (Bok and Keller, *Eukaryot Cell*. 2004, April 3(2), 527-352). AflR AflS/J are a conserved pair of regulatory genes found in many secondary metabolite clusters.

ST is the penultimate precursor of aflatoxin (AF), which is produced by the related species *A. flavus* and *A. parasiticus*. AflR was first identified in *A. flavus* (Payne et al. (1993) Appl. Environ Microbiol. 59, 156-162) and subsequently in *A. parasiticus* (Chang et al. (1993) Appl. Environ. Microbiol. 59, 3273-3279). AflR regulates the expression of the AF cluster genes in both *A. flavus* and *A. parasiticus* in a manner similar to the stc genes. aflR is not constitutively expressed in these three species and is regulated through a complex interaction with G protein/cAMP/protein kinase A signal transduction pathway also involved in asexual spore development (Flicks et al., 1997; Shimizu and Keller, 2001).

The term "*A. nidulans* strain TPMW2.3," as used herein, refers to a strain of *A. nidulans* with its endogenous ST cluster removed but with aflR/aflJ placed back into the strain, in the ST cluster location in the genome, under the control of a promoter that is inducible by nitrate and repressible by ammonium and certain amino acids, such as glutamine, thereby allowing controlled aflR/aflJ gene expression based on culture conditions. In one embodiment, the repression is also possible by amino acids such as glutamine etc. In one embodiment, one may create a gene construct using the nitrate inducible promoter niiA/niaD upstream of the aflR and aflJ genes which are upstream of a selection marker.

The term "filamentous fungi," as used herein, refers to any fungus that has filamentous structure from the Phylum Ascomycota. In certain embodiments, filamentous fungi may include *A. nidulans*.

The term "Amino acid sequence," as used herein, refers to an oligopeptide, peptide, polypeptide, or protein sequence, and fragment thereof. Where "amino acid sequence" is recited herein to refer to a particular amino acid sequence, "amino acid sequence", and like terms, are not meant to limit the amino acid sequence to the complete amino acid sequence referenced but shall be understood to include fragments of the complete amino acid sequence. The term shall further encompass synthetic molecules as well as those occurring naturally. The term "portion" or "fragment", as used herein, with regard to an amino acid sequence, specifically refers to segments of that amino acid sequence which are not naturally occurring as fragments and would not be found in the natural state. The segments may range in size from five amino acid residues to the entire amino acid sequence minus one amino acid. Thus, a polypeptide "comprising at least a portion of the amino acid sequence of one SEQ ID NO" or "including an amino acid sequence as set forth in one SEQ ID NO or fragments thereof" encompasses the full-length amino acid sequences and segments thereof.

The term "biologically active", as used herein, refers to a protein, polypeptide, amino acid sequence, or nucleotide sequence encoding a product having structural, regulatory, or biochemical functions of a naturally occurring molecule. Preferably, a biologically active fragment of SM genes will have the secondary metabolite gene cluster regulatory capabilities of a naturally occurring SM molecule disclosed herein.

"Nucleic acid sequence" or "nucleotide sequence" or polynucleotide sequence", as used herein, refers to an oligonucleotide, nucleotide, or polynucleotide, and fragments thereof, and to DNA or RNA of genomic or synthetic origin which may be single- or double-stranded, and represent the sense or antisense strand. Where "nucleic acid sequence" or "nucleotide sequence" or polynucleotide sequence" is recited herein to refer to a particular nucleotide sequence, "nucleotide sequence", and like terms, are not meant to limit the nucleotide sequence to the complete nucleotide sequence referenced but shall be understood to include fragments of the complete nucleotide sequence. In this context, the term "fragment" may be used to specifically refer to those nucleic acid sequences which are not naturally occurring as fragments and would not be found in the natural state. Generally, such fragments are equal to or greater than 15 nucleotides in length, and most preferably includes fragments that are at least 60 nucleotides in length. Such fragments find utility as, for example, probes useful in the detection of nucleotide sequences encoding SM or ST gene.

The term "sample", as used herein, is used in its broadest sense. A biological sample suspected of containing nucleic acid encoding SM or ST gene, or fragments thereof, or SM or ST gene itself may comprise a bodily fluid, extract from a cell, chromosome, organelle, or membrane isolated from a cell, a cell, genomic DNA, RNA, or cDNA (in solution or bound to a solid support, a tissue, a tissue print, and the like).

The terms "polypeptide", "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. The term also includes variations on the traditional peptide linkage joining the amino acids making up the polypeptide. Where the terms are recited herein to refer to a polypeptide, peptide or protein of a naturally occurring protein molecule, the terms are not meant to limit the polypeptide, peptide or protein to the complete, native amino acid sequence associated with the recited protein molecule but shall be understood to include fragments of the complete polypeptide. The term "portion" or "fragment", as used herein, with regard to a protein or polypeptide refers to segments of that polypeptide which are not naturally occurring as fragments in nature. The segments may range in size from five amino acid residues to the entire amino acid sequence minus one amino acid. Thus, a polypeptide "as set forth in one SEQ ID NO or a fragment thereof" encompasses the full-length amino acid sequence set forth in one SEQ ID NO as well as segments thereof. Fragments of SM or ST gene preferably are biologically active as defined herein.

The terms "nucleic acid" or "oligonucleotide" or "polynucleotide" or grammatical equivalents herein refer to at least two nucleotides covalently linked together. A nucleic acid of the present invention is preferably single-stranded or double stranded and will generally contain phosphodiester bonds, although in some cases, as outlined below, nucleic acid analogs are included that may have alternate backbones, comprising, for example, phosphoramide (Beaucage et al. (1993) *Tetrahedron* 49:1925) and references therein; Letsinger (1970) *J. Org. Chem.* 35:3800; Sprinzi et al. (1977) *Eur. J. Biochem.* 81: 579; Letsinger et al. (1986) *Nucl. Acids Res.* 14: 3487; Sawai et al. (1984) *Chem. Lett.* 805, Letsinger et al. (1988) *J. Am. Chem.* Soc. 110; 4470; and Pauwels et al. (1986) *Chemica Scripta* 26: 1419), phosphorothioate (Mag et al. (1991) *Nucleic Acids Res.* 19:1437; and U.S. Pat. No. 5,644,048), phosphorodithioate (Briu et al. (1989) *J. Am. Chem. Soc.* 111: 2321, O-methylphophoroamidite linkages (see Eckstein, *Oligonucleotides and Analogues: A Practical Approach*, Oxford University Press), and peptide nucleic acid backbones and linkages (see Egholm (1992) *J. Am. Chem. Soc.* 114:1895; Meier et al. (1992) *Chem. Int. Ed. Engl.* 31: 1008; Nielsen (1993) *Nature,* 365: 566; Carlsson et al. (1996) *Nature* 380: 207). Other analog nucleic acids include those with positive backbones (Denpcy et al. (1995) *Proc. Natl. Acad. Sci. USA* 92: 6097; non-ionic backbones (U.S. Pat. Nos. 5,386,023, 5,637,684, 5,602,240, 5,216,141 and 4,469.863; Angew. (1991) *Chem. Intl. Ed. English* 30: 423; Letsinger et al. (1988) *J. Am. Chem. Soc.* 110:4470; Letsinger et al. (1994) *Nucleoside & Nucleotide* 13:1597; Chapters 2 and 3, ASC Symposium Series 580, "Carbohydrate Modifications in Antisense Research". Ed. Y. S. Sanghui and P. Dan Cook; Mesmaeker et al. (1994). *Bioorganic & Medicinal Chem. Lett.* 4: 395; Jeffs et al. (1994) *J. Bimolecular NMR* 34:17: *Tetrahedron Lett.* 37:743 (1996) and non-ribose backbones, including those described in U.S. Pat. Nos. 5,235,033 and 5,034,506, and Chapters 6 and 7, ASC Symposium Series 580, *Carbohydrate Modifications in Antisense Research*, Ed. Y. S. Sanghui and P. Dan Cook. Nucleic acids containing one or more carbocyclic sugars are also included within the definition of nucleic acids (see Jenkins et al. (1995), *Chem. Soc. Rev.* pp 169-176). Several nucleic acid analogs are described in Rawls, C & E News Jun. 2, 1997 page 35. These modifications of the ribose-phosphate backbone may be done to facilitate the addition of additional moieties such as labels, or to increase the stability and half-life of such molecules in physiological environments. As used herein, oligonucleotide is substantially equivalent to the terms "amplimers", "primers", "oligomers", and "probes", as commonly defined in the art.

The term "heterologous" as it relates to nucleic acid sequences such as coding sequences and control sequences, denotes sequences that are not normally associated with a region of a recombinant construct, and/or are not normally associated with a particular cell. Thus, a "heterologous" region of a nucleic acid construct is an identifiable segment of nucleic acid within or attached to another nucleic acid molecule that is not found in association with the other molecule in nature. For example, a heterologous region of a construct could include a coding sequence flanked by sequences not found in association with the coding sequence in nature. Another example of a heterologous coding sequence is a construct where the coding sequence itself is not found in nature (e.g., synthetic sequences having codons different from the native gene). Similarly, a host cell transformed with a construct which is not normally present in the host cell would be considered heterologous for purposes of this invention.

A "coding sequence" or a sequence which "encodes" a particular polypeptide (e.g. a methyltransferase, etc.), is a nucleic acid sequence which is ultimately transcribed and/or translated into that polypeptide in vitro and/or in vivo when placed under the control of appropriate regulatory sequences. In certain embodiments, the boundaries of the coding sequence are determined by a start codon at the 5' (amino) terminus and a translation stop codon at the 3' (carboxy) terminus. A coding sequence can include, but is not limited to, cDNA from procaryotic or eucaryotic mRNA, genomic DNA sequences from procaryotic or eucaryotic DNA, and even synthetic DNA sequences. In preferred embodiments, a transcription termination sequence will usually be located 3' to the coding sequence.

The term "ortholog" refers to genes or proteins which are homologs via speciation, e.g., closely related and assumed to have common descent based on structural and functional considerations. Orthologous proteins function as recognizably the same activity in different species.

Expression "control sequences" or "regulatory elements" refers collectively to promoter sequences, ribosome binding sites, polyadenylation signals, transcription termination sequences, upstream regulatory domains, enhancers, and the like, which collectively provide for the transcription and translation of a coding sequence in a host cell. Not all of these control sequences need always be present in a recombinant vector so long as the desired gene is capable of being transcribed and translated.

"Recombination" refers to the reassortment of sections of DNA or RNA sequences between two DNA or RNA molecules. "Homologous recombination" occurs between two DNA molecules which hybridize by virtue of homologous or complementary nucleotide sequences present in each DNA molecule.

The terms "stringent conditions" or "hybridization under stringent conditions" refers to conditions under which a probe will hybridize preferentially to its target subsequence, and to a lesser extent to, or not at all to, other sequences. "Stringent hybridization" and "stringent hybridization wash conditions" in the context of nucleic acid hybridization experiments such as Southern and northern hybridizations are sequence dependent, and are different under different environmental parameters. An extensive guide to the hybridization of nucleic acids is found in Tijssen (1993) *Laboratory Techniques in Biochemistry and Molecular Biology—Hybridization with Nucleic Acid Probes part 1 chapter 2 Overview of principles of hybridization and the strategy of nucleic acid probe assays*, Elsevier, New York. Generally, highly stringent hybridization and wash conditions are selected to be about 5° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Very stringent conditions are selected to be equal to the $T_m$ for a particular probe.

"Expression vectors" are defined herein as nucleic acid sequences that are direct the transcription of cloned copies of genes/cDNAs and/or the translation of their mRNAs in an appropriate host. Such vectors can be used to express genes or cDNAs in a variety of hosts such as bacteria, bluegreen algae, plant cells, insect cells and animal cells. Expression vectors include, but are not limited to, cloning vectors, modified cloning vectors, specifically designed plasmids or viruses. Specifically designed vectors allow the shuttling of DNA between hosts, such as bacteria-yeast or bacteria-animal cells. An appropriately constructed expression vector preferably contains: an origin of replication for autonomous replication in a host cell, a selectable marker, optionally one or more restriction enzyme sites, optionally one or more constitutive or inducible promoters. In preferred embodiments, an expression vector is a replicable DNA construct in which a DNA sequence encoding SM or ST gene or a fragment thereof is operably linked to suitable control sequences capable of effecting the expression of the products in a suitable host. Control sequences include a transcriptional promoter, an optional operator sequence to control transcription and sequences which control the termination of transcription and translation, and so forth.

An "allele" or "allelic sequence", as used herein, is an alternative form of the gene encoding the nucleotide sequences of the specific gene obtained from *Aspergillus nidulans*. Alleles may result from at least one mutation in the nucleic acid sequence and may result in altered mRNAs or polypeptides whose structure or function may or may not be altered. Any given natural or recombinant gene may have none, one, or many allelic forms. Common mutational changes which give rise to alleles are generally ascribed to natural deletions, additions, or substitutions of nucleotides. Each of these types of changes may occur alone, or in combination with the others, one or more times in a given sequence.

As used herein, the term "exon" refers to a nucleic acid sequence found in genomic DNA that is bioinformatically predicted and/or experimentally confirmed to contribute contiguous sequence to a mature mRNA transcript.

A "coding sequence" or a sequence which "encodes" a particular polypeptide (e.g. a methyltransferase, etc.), is a nucleic acid sequence which is ultimately transcribed and/or translated into that polypeptide in vitro and/or in vivo when placed under the control of appropriate regulatory sequences. In certain embodiments, the boundaries of the coding sequence are determined by a start codon at the 5' (amino) terminus and a translation stop codon at the 3' (carboxy) terminus. A coding sequence can include, but is not limited to, cDNA from procaryotic or eucaryotic mRNA, genomic DNA sequences from procaryotic or eucaryotic DNA, and even synthetic DNA sequences. In preferred embodiments, a transcription termination sequence will usually be located 3' to the coding sequence.

"Amplification", as used herein, refers to the production of additional copies of a nucleic acid sequence and is generally carried out using polymerase chain reaction (PCR)

technologies well known in the art (Dieffenbach. C. W. and G. S. Dveksler (1995) PCR Primer, a Laboratory Manual. Cold Spring Harbor Press, Plainview, N.Y.).

"Deletion", as used herein, refers to a change in the amino acid or nucleotide sequence and results in the absence of one or more amino acid residues or nucleotides.

An "insertion" or "addition", as used herein, refers to a change in an amino acid or nucleotide sequence resulting in the addition of one or more amino acid residues or nucleotides, respectively, as compared to the naturally occurring molecule.

The term "gene cluster." as used herein, refers to a totality of DNA coding for polypeptides required to catalyze a certain biochemical pathway. A gene cluster can be on a single DNA molecule, or can be on multiple DNA molecules, e.g. in form of a DNA library.

Abbreviations used herein include aa, amino acid; MMG, minimal media glucose; MMT, minimal media threonine; OE, over expression; LB, Luria-Bertani; nt, nucleotide; ORF, open reading frame; PCR, polymerase chain reaction; PEG, polyethyleneglycol; R, resistant; WT, wild-type; and TS, temperature sensitive.

III. The Invention

In one aspect, the present invention are inducible expression systems for producing fungal secondary metabolites and methods of using such systems. In one embodiment, the inducible expression systems comprise a strain of genetically modified organisms.

In one specific embodiment, the genetically modified organism are fungi, such as filamentous fungi. Applicants designed a strain of the GRAS organism *Aspergillus nidulans* that contains a genetic construct utilizing the regulatory genes from the sterigmatocystin (ST) gene cluster, aflR and aflJ for inducible expression of genetic pathways that produce SMs.

Throughout the application, GRAS *Aspergillus nidulans* are used as examples for the purpose of demonstration. Applicants envision that any type of genetically amenable filamentous fungi may be used for the present invention.

In one embodiment, the auxotrophic markers may need to be adapted and it must in general be possible to transform the species. The heterologous cluster genes may be derived from any filamentous fungus of the Division/Phylum Ascomycota.

In one embodiment, the strain of the GRAS organism *Aspergillus nidulans* comprises a genetic construct which allows for expression of the positive acting transcriptional elements of the sterigmatocystin (ST) gene cluster, aflR and aflJ. The sequences for homologous genes can also be derived from *A. versicolor, A. flavus* or *A. parasiticus* that harbor either the sterigmatocystin or the aflatoxin gene cluster. In theory, any activating transcription factor from a given gene cluster can be used instead of the aflR/aflJ sequences.

One example of such a strain of the GRAS organism *Aspergillus nidulans* is the *A. nidulans* strain TPMW2.3. FIGS. 1A and 1B are diagrams and graphs showing the structure and construct of Inducible aflR/aflJ *Aspergillus nidulans* strain. The *A. nidulans* strain TPMW2.3 is derived from *A. nidulans* WT. The *A. nidulans* strain TPMW2.3 contains an $NO_3^-$-inducible aflR/aflJ construct. Specifically, the *A. nidulans* strain TPMW2.3 is derived from L08030 (pyrG-, pyroA-, riboA- are three selection markers). ST cluster is deleted. niiA/niaD promoter (that drives expression of aflR/aflJ) is integrated in ST cluster region using selection marker 1 (pyroA). The strain has green spores and riboflavin and uracil, uridine auxotrophy.

In one embodiment, inducible aflR/aflJ *Aspergillus nidulans* strain such as strain TPMW2.3 forms after endogenous ST cluster in the wild type *A. nidulans* are removed and the regulatory genes aflR/aflJ are placed back into the wild type *A. nidulans*. In particular, niiA/niaD promoter is inducible by nitrate and repressible by ammonium. Therefore, the expression of aflR/aflJ may be controlled on the basis of culture conditions, e.g., either nitrate or ammonium. FIG. 1B demonstrates inducibility of aflR/aflJ expression by nitrate and repressibility of aflR/aflJ expression by ammonium. The nitrate inducible promoter region can be replaced by any inducible promoter known to work in filamentous fungi, such as but not limited to: the acetate-inducible promoters (acu-3, acu-5, acu-8, and acu-9) (Mizote et al., 1996), the xylase inducible promoter exlA (Gouka et al., 1996), the alcohol inducible alcA promoter (Waring et al., 1997), the starch inducible glaA promoter (Fowler et al., 1990), the inulin inducible promoter inuE (Yuan et al., 2008), the calcium carbonate and hydrogen peroxide inducible promoter catR (Sharma et al., 2012), the thiamine promoter thiA (Shoji et al., 2005), the human estrogen receptor system hERα (Pachlinger et al., 2005), and the tetracycline resistance operon (Tet-ON) (Vgt et al., 2005; Meyer et al., 2011).

In one aspect, the present invention is a method of using the above systems to produce secondary metabolites. In one embodiment, the method comprises the steps of (a) obtaining a strain of a fungal organism capable of producing ST; (b) deleting the ST gene cluster from the strain of the fungal organism; (c) adding back the regulatory genes aflR and aflJ in the ST cluster location in the genome of the strain under control of a first promoter that is inducible by nitrate and repressible by ammonium; (d) creating plasmids by using a second promoter; (e) fusing a target SM gene cluster into the plasmids; and (f) transforming the strain of the fungal organism with the plasmids, inducing with nitrate and producing the fungal SM.

In one embodiment of the present invention, methods of increasing the amount of a secondary metabolite as described and claimed herein are practiced in an *Aspergillus* species such as *A. nidulans. A. flavus* or *A. terreus*. Secondary metabolites increased by the methods include but are not limited to carotenoids and spiroquinazoline alkaloids.

As discussed above, any strain of filamentous fungi capable of producing ST may be used for the present invention. In one embodiment, any strain of *A. nidulans* capable of producing ST may be used to produce aflR/aflJ inducible *A. nidulans* strain. For example, a strain of *A. nidulans*, derived from L08030 with pyrG-, pyroA-, riboA- three selection markers was initially used in the present invention.

After the strain of a fungal organism capable of producing ST was obtained, the endogenous ST cluster of the strain is removed. The ST gene cluster contains 26 distinct genes including the regulatory genes aflR and aflJ and the enzymatic genes stcA-stcW (see FIG. 1A). It is known that aflR/aflJ are responsible for ST production (Brown, et al., 1996; Yu, et al., 1996). AflR and AflJ expression activates src expression. It is known that the ST cluster is the most strongly regulated SM cluster in *A. nidulans* with up to ca. 1-10% of all transcripts. In one embodiment of the present invention, Applicants take advantage of the power of aflR/aflJ induction of sic promoters to produce novel and valuable SMs.

Any suitable method as appreciated by one skilled in the art may be used to remove the endogenous ST cluster from the strain of the fungal organism. The exemplary methods may include PEG-mediated transformation using homologous recombination.

After removal of the endogenous ST cluster, the regulatory genes aflR and aflJ are added back in the ST cluster location in the genome of the strain. In one embodiment, this step is under the control of a first promoter that is inducible by nitrate and repressible by ammonium. One specific example of the first promoter is the nitrate inducible promoter niiA/niaD. In particular, the nitrate inducible promoter niiA/niaD is placed upstream of the aflR and aflJ genes which are placed upstream of a selection marker. Other inducible promoters as mentioned above are expected to work are expected to account for aflR/aflJ expression similarly.

Any suitable marker as appreciated by one skilled in the art may be used as the selection marker. In one embodiment of the present invention, the selection marker is pyroA.

After niiA/niaD promoter (that drives expression of aflR/aflJ) is integrated, plasmids are created by using a second promoter. In one embodiment, the second promoter may be any gene of the 26 genes from the ST gene cluster (see FIG. 1). Specifically, the 26 genes from the ST gene cluster comprise the regulatory genes aflR and aflJ and the enzymatic genes stcA-stcW. The same induction is anticipated for the stc promoters from *A. versicolor* and the aft promoters from *A. flavus* and *A. parasiticus*.

In one embodiment, the present invention provides methods for testing the expression of the 26 different ST genes as the second promoters by aflR/aflJ in the genetically modified strain (e.g., *A. nidulans* strain TPMW2.3). Specifically, the present invention provides methods for identifying nitrate inducible ST promoters. For example, one can create test plasmids wherein any of the 26 different ST genes may be fused into a reporter gene. A report gene may include any gene which can convey viability upon expression.

In one embodiment, one can subsequently transform the genetically modified strain (e.g., *A. nidulans* strain TPMW2.3) with the test plasmids and select transformants that could grow under certain media conditions (using selection markers) after induction with nitrate. The only way these transformed organisms could grow was that the ST promoters were being strongly affected by aflR and aflJ. One can thus identify the genes as nitrate inducible ST promoters.

Specifically. Applicants identified eight ST genes as nitrate inducible ST promoters, which are useful for aflR/aflJ induced expression of selection markers. The eight nitrate inducible ST promoters include stcA, stcB, stcC, AN11017, stcN, stcQ, stcV and stc W.

After plasmids are created by using a second promoter, a target SM gene cluster is provided and fused into the plasmids. Any SM gene cluster may be used as the target SM gene cluster. Preferably, suitable SM gene clusters may include those corresponding to SMs which could not be abundantly produced from chemical synthesis or from nature existing organisms.

The SM gene cluster to be expressed is fused into the plasmids. Any method as appreciated by one skilled in the art may be used to fuse the SM gene cluster to the plasmids. In one preferred embodiment, the method for fusing the SM gene cluster to the plasmids is Yeast transformation, e.g., one-step recombinational cloning of multiple fragments.

After fusion of a target SM gene into the plasmids, the genetically modified strain is transformed with the plasmids. In one specific embodiment, the transformation is induced with nitrate. Expression of the second promoter. e.g., one ST gene, preferably one nitrate inducible ST promoter, can activate expression of the target SM gene. Thus, the fungal SM corresponding to the target SM gene is produced. In one embodiment, nitrate inducible aflR/aflJ transcription factors induce gene expression of SM cluster genes fused to ST promoters, thereby leading to the production of a new metabolite.

In one embodiment, each of the 26 ST genes may be used as a second promoter. These ST second promoters are fused to novel SM cluster genes by one-step yeast recombinational cloning with the resultant construct transformed into the *A. nidulans* aflR/aflJ strain.

In one embodiment, the methods of the present invention may be used to produce SMs which are either previously-unknown. Applicants envision that the use of inducible ST promoters for expression of unknown SM cluster genes would allow for simultaneous and specific co-expression of all biosynthetic enzyme-encoding genes. Thus, previously-unknown SMs may be produced.

In another embodiment, the methods of the present invention may be used to produce known SMs. These known SMs cannot be effectively produced by using any previous method.

Furthermore. Applicants envision that the inducibility of gene expression would allow production of potential antifungal SMs because the genes responsible for their production can specifically be turned on at later growth stages when significant fungal biomass has accumulated. It is well-known that ST genes are the most highly expressed genes in *A. nidulans* and use of their promoters will result in high expression of novel SMs.

For example, the present method may include the following specific steps: PCR of all Promoters, PCR of pyrG gene, linearize backbone vector including flanks for the yA gene (responsible for turning spores from yellow to green); Yeast transformation (one-step recombinational cloning of multiple fragments); Plasmid isolation and transformation into *E. coli* (high copy number); Picking of single colonies, Plasmid Isolation. Test restriction; Cut out deletion fragment, transformation into *A. nidulans* (TPMW2.3); Select for yellow colonies, test growth on $NO_3^-$ and $NH_4^+$ (+/−U/U); and Confirm integration by PCR.

In one embodiment, the target SM gene in the present invention may be from any organism, preferably any fungus, more preferably any filamentous fungus from the Division/Phylum Ascomycota. FIGS. 1A, 1B, 2A, 2B, 2C, 3, 4, 5A, 5B, 5C, 5D, 6A, 6B, 7, 8A, 8B, 9A, 9B, and 9C illustrate one example of the present invention. Specifically, to validate the system for secondary metabolite production, Applicants built test plasmids to contain the ST promoters that showed effective aflR/aflJ inducibility and incorporated an SM gene cluster from *A. terreus, Fusarium fujikuori*, and *A. flavus* into the test plasmid. Applicants successfully transformed TPMW2.3 with the test plasmids, induced with nitrate and measured both gene expression of the gene cluster and the resulting SM produced.

FIG. 9, confirms the inducibility of our system demonstrated in previous figures, while further showing that we can use the system to express genes from different genera in *A. nidulans*. Specifically, FIG. 9 shows successful product formation (ß-carotene) using a *Fusarium* gene.

In one embodiment, the present invention provides methods and systems for enhancing expression and testing of the second promoters as discussed above. Applicants envision that a mutated version of aflR could greatly increase the production of ST promoters and, hence, the SM clusters fused to them. In one specific embodiment, the mutated version of aflR is aflR$^{S323A,S381A,S382A}$.

Applicants previously found that that aflR levels are controlled post-transcriptionally by phosphorylation by protein kinase A (PkaA). If the three PkaA phosphorylation sites were mutated as in the aflR$^{S323A,S381A,S382A}$, allele, then aflR remains active, ST promoter expression increases 40 fold with resultant similar increase in ST production (see Shimizu, Hicks, et al., 2003).

Applicants envision that methods for enhancing expression and testing of the second promoters will include similar steps to the methods as discussed above. The methods of enhancement would focus on construction of a new *A. nidulans* strain harboring a dominant-active copy of the transcriptional enhancer AflR. In one embodiment, the new *A. nidulans* strain would be mostly similar to those (e.g., *A. nidulans* strain TPMW2.3) as discussed above other than the structure of its AflR. The AflR in the new *A. nidulans* strain is a mutated version of AflR. In one specific embodiment, the mutations of the AflR in the new *A. nidulans* strain comprise S323A, S381A, S382A.

The mutated version of aflR may be produced through any suitable method as appreciated by one skilled in the art. In one embodiment, the new dominant active version of aflR will be achieved by site directed mutation of certain amino acids uncoupling aflR from post-transcriptional control mechanisms.

EXAMPLES

The following examples are offered for illustrative purposes only, and are not intended to limit the scope of the present invention in any way. Indeed, various modifications of the invention in addition to those shown and described herein will become apparent to those skilled in the art from the foregoing description and fall within the scope of the appended claims.

Inducible Expression System for Production of Novel Fungal Secondary Metabolites As an example for the present invention, Applicants designed a strain of the GRAS organism *Aspergillus nidulans* that contains a genetic construct which allows for expression of the positive acting transcriptional elements of the sterigmatocystin (ST) gene cluster, aflR and aflJ. The ST gene cluster contains 26 distinct genes and it is known that AflR/AflJ are responsible for ST production (Brown, et al., 1996; Yu et al., 1996). Applicants constructed a strain of *A. nidulans* with its endogenous ST cluster removed but with aflR/aflJ placed back into the strain under the control of a promoter that is inducible by nitrate and repressible by ammonium (Johnstone, et al., 1990), thereby allowing controlled aflR/aflJ expression based on culture conditions.

Figure 3:
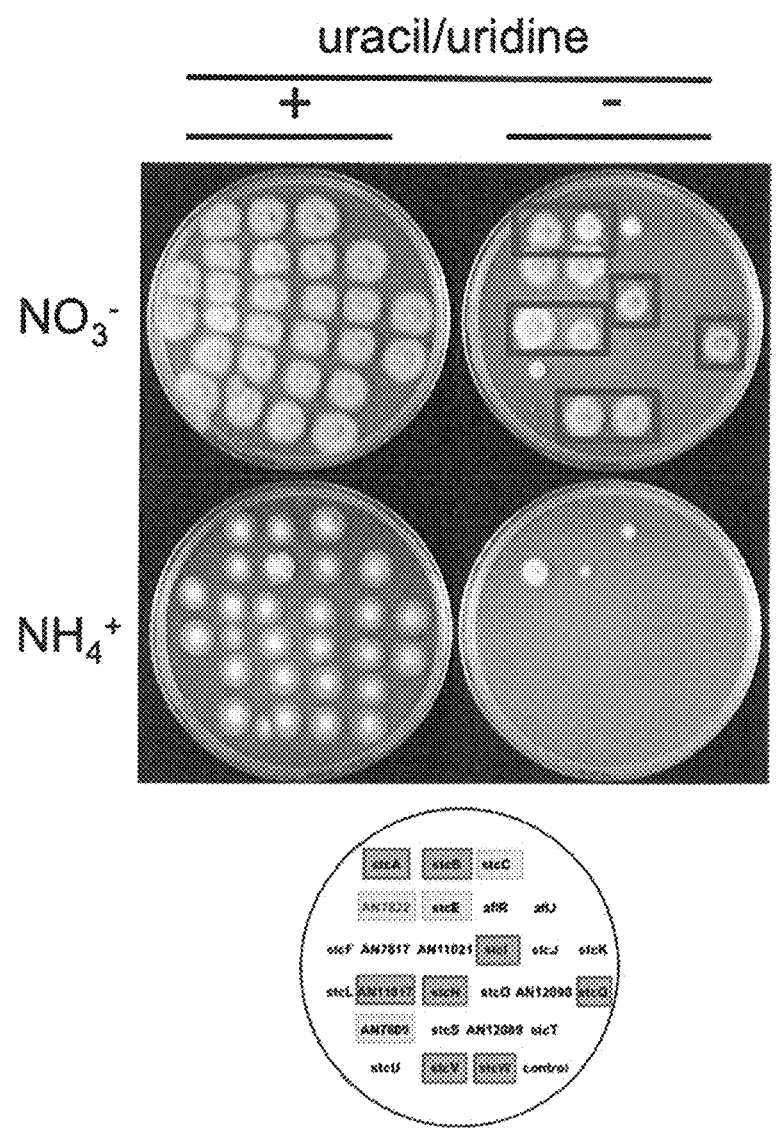
FIG. 3 is a picture showing selection of AflR/AflJ-inducible ST promoters. The images on the left shows media allowing for growth of all transformants (expression of pyrG is not needed as uracil & uridine (U/U) is added). The images on the right show selection media for strains that can only grown when AflR/AflJ is induced by $NO_3^-$ and are able to drive the expression of the respective ST promoter. The promoter regions for the genes stcA, stcB, stcI, AN11017, stcN, stcQ, stcV, and stcW show inducibility by $NO_3^-$ and simultaneous repression by $NH_4^+$.
Figure 4:
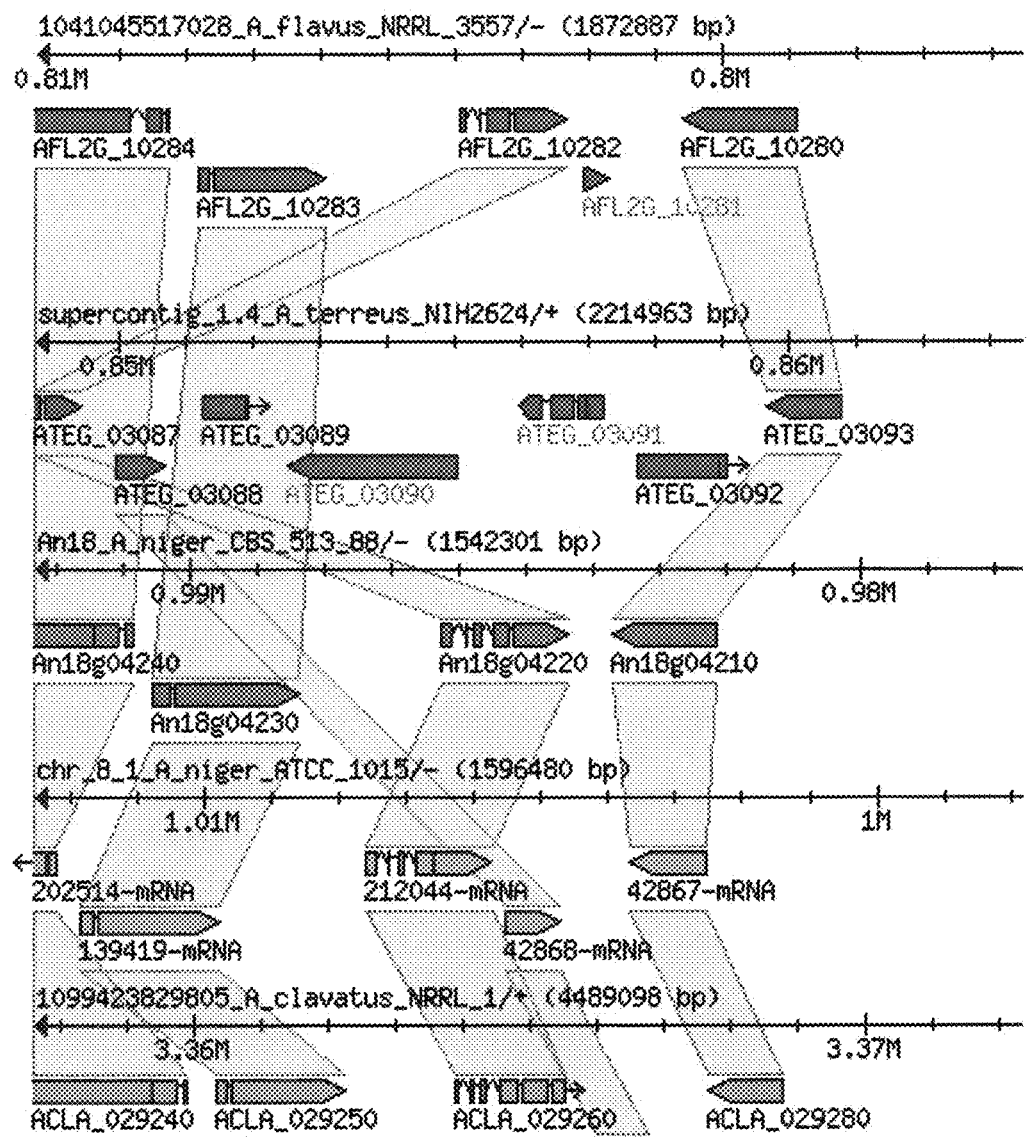
FIG. 4 is a diagram showing test Cluster from *A. terreus*. Based on synteny the 4 genes ATEG_03089-92 are not present in any other *Aspergillus* spp. These 4 genes include ATEG_03089:Hydrolase; ATEG_03090:NRPS-like; ATEG_03091:O-Methyltransferase; and ATEG_03092: DMATS.
Figure 6A:
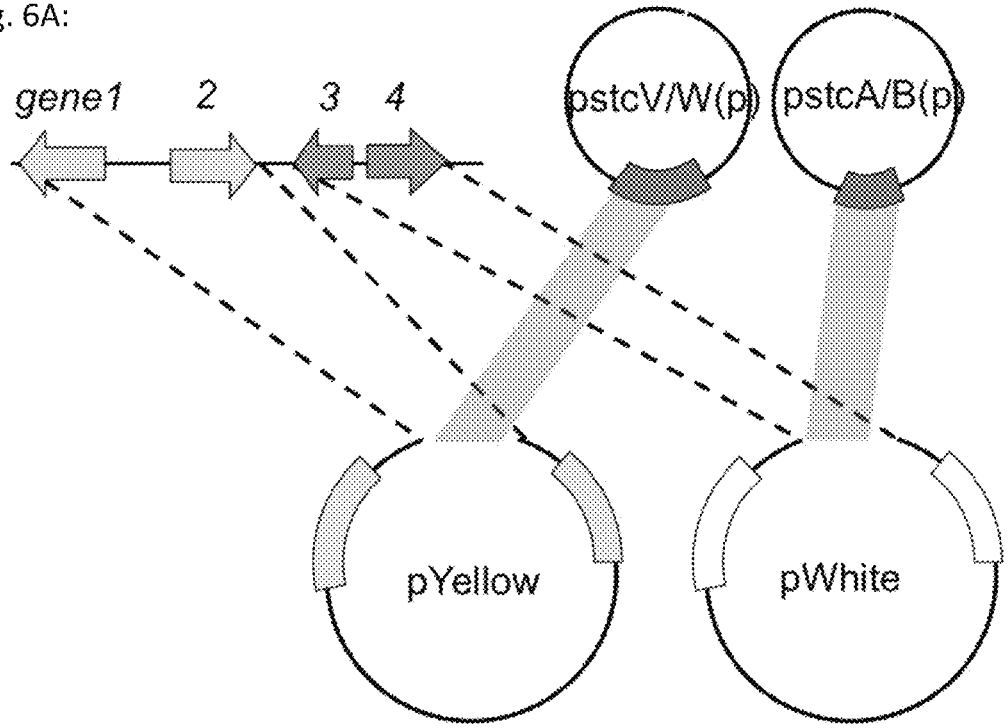
FIGS. 6A and 6B are diagrams and graphs showing cloning of vectors used for inducible expression system for production of novel fungal secondary metabolites.
Figure 6B:
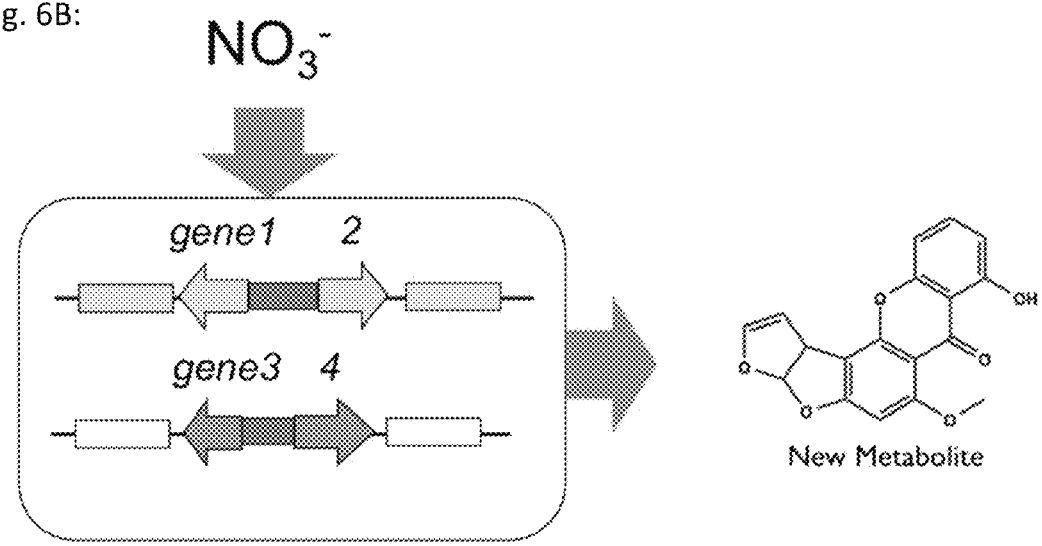
Figure 7:
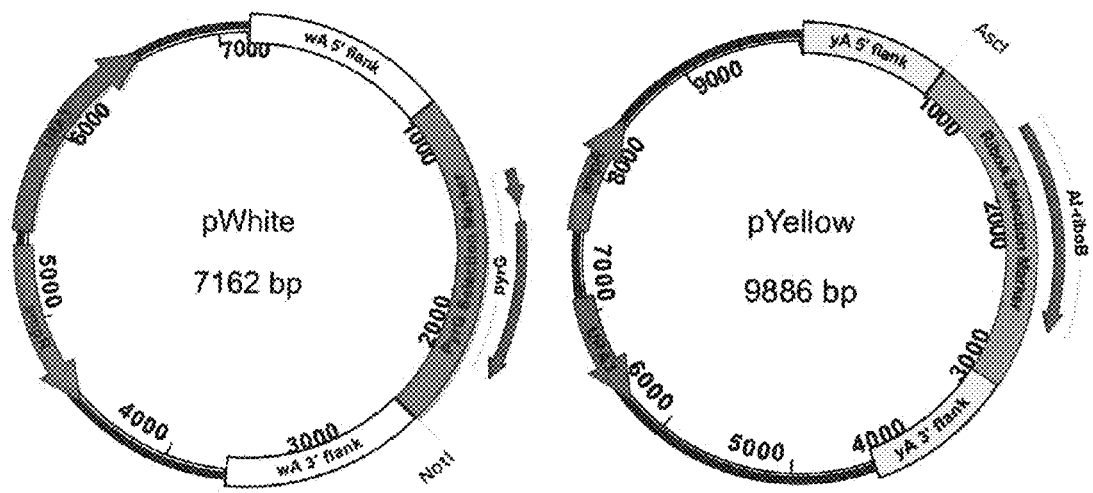
FIG. 7 are diagrams of the plasmids pWhite and pYellow. Each plasmid harbors genetic elements for selection in *Saccharonmyces cerevisiae* (URA3) and *Escherichia coli* (ampR), respectively. Plasmid pWhite contains the flanks of the *A. nidulans* gene wA (turning yellow into green spores) and the pyrG gene (conveying uracil/uridine prototrophie). The plasmid can be linearized by the restriction enzyme NotI. Plasmid pYellow contains the flanks of the *A. nidulans* gene yA (turning yellow into green spores) and the riboA gene (conveying riboflavin prototrophie). The plasmid can be linearized by the restriction enzyme Asc1.
Figure 8A:
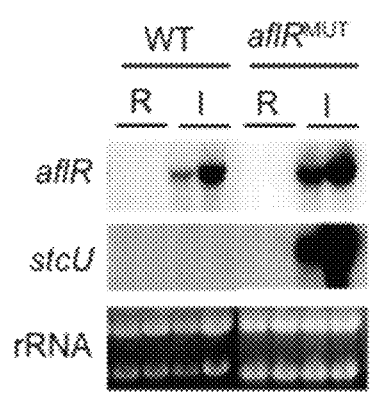
FIGS. 8A and 8B are graphs showing Enhanced stcU expression and ST production in a strain expressing a $aflR^{S323A,S381A,S382A}$ under inducing conditions.
Figure 8B:
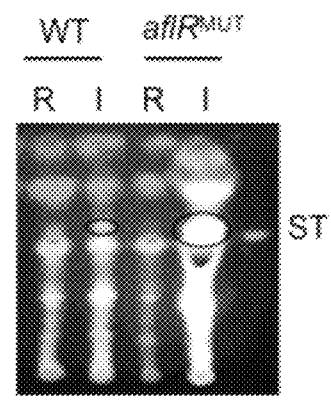
Figure 9A:
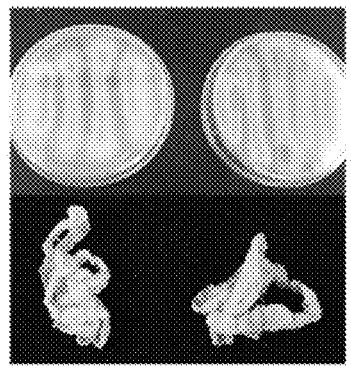
FIGS. 9A, 9B and 9C are pictures and graphs showing the ß-carotene expressing strain TJSF1.1 compared to the control strain TPMW8.2 complemented with empty plasmids depicted in FIG. 7.
Figure 9B:
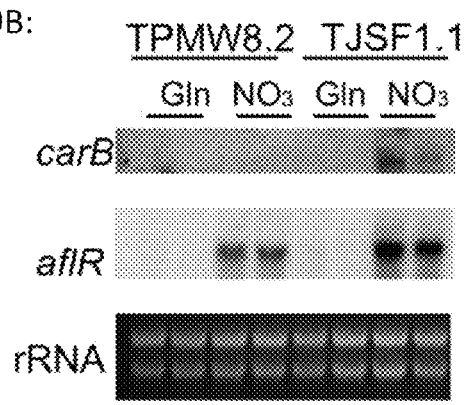
Figure 9C:
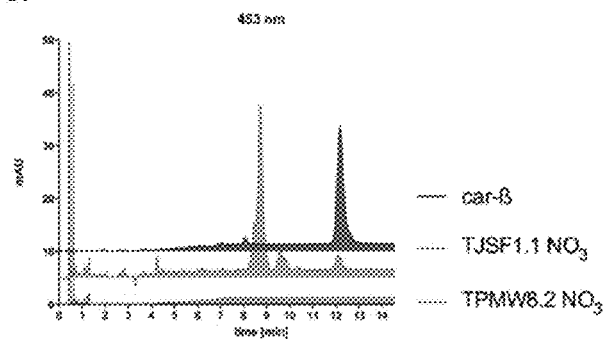

Applicants tested the expression of the 26 different ST promoters by AflR/AflJ in this strain and identified nitrate inducible ST promoters by fusing them to a reporter gene conveying viability upon expression (FIGS. 3 and 5).

Previous strategies on activating fungal SMs have focused mainly on 1) activating endogenous gene clusters by either over-expressing the pathway-specific transcription factor or manipulating global regulators and 2) expressing the entire gene cluster in a heterologous host. Although successful in some cases, these strategies have significant disadvantages. As not all fungal species are amenable to genetic manipulation, strategies that focus on endogenous activation are impossible in these species. If genetic manipulations are possible, activation of an otherwise silent cluster still depends the presence of a cluster-specific transcription factor. However, not all SM clusters contain transcription factors. Another major disadvantage of overexpressing SMs is that many SMs are toxic to the host fungus, thereby making the isolation of significant amounts of the desired compound difficult.

Approaches expressing fungal gene clusters in heterologous hosts (mainly *Saccharomyces cerevisiae* or *Aspergillus* spp.) focused on amplification of the entire gene cluster including native promoters. Although these approaches led to expression of the targeted gene clusters in some cases, the use of native promoters cannot guarantee controlled activation of the genes. As a result, those clusters still remain silent in the new host in most cases. Exchange of native promoters with constitutively expressing promoters for an entire gene cluster is unfeasible up to now. Although a few constitutively promoters for fungal species are commonly used, not enough promoters are known in order to fuse all cluster genes to unique promoters. The use of the same promoter sequence for several genes of a cluster is impossible due to the yeast cloning technique applied for assembling the gene cluster in a suitable plasmid. Cloning of gene clusters is achieved by PCR-based amplification of the desired DNA region and subsequent yeast recombination-based cloning.

In general, the gene cluster is amplified in several 1-2 kb pieces by use of primers with short overlapping 5'-overhangs. These fragments are co-transformed with a linearized shuttle vector into yeast cells for assembly by its recombination machinery. The yeast recombination-based system requires unique promoters be used for each gene to be expressed in the plasmid. The use of the same promoter sequences would result in incorrect assembly of the desired plasmid.

The present invention provides important advantages to these existing technologies: 1) By use of individual promoter sequences, one-step yeast recombination-based cloning of genes fused to the inducible promoters is possible; 2) The *A. nidulans* strain used for heterologous expression of the gene cluster of choice has eight of its endogenous SM gene clusters deleted thereby abolishing production of interfering compounds and hence facilitating identification and isolation of the newly produced chemicals; 3) The inducibility of gene expression in our system will allow production of potential anti-fungal SMs as the genes responsible for their production can specifically be turned on at later growth stages when significant fungal biomass has accumulated.

SMs are a remarkably rich source of medically useful compounds and/or can be used as chemical scaffolds in semi-synthetic chemistry to become useful. Fungal SMs, in particular, have included a number of important compounds including, among others, antibacterials such as penicillin, cephalosporin, the hypercholesterolaemic agent lovastatin and other statins, immunosuppressants such as cyclosporine, as well as antifungals. According to the latest World Health Organization (WHO) report affective pharmaceuticals are limited and anti-microbials constantly rendered useless due to emergence of resistant microbes. Continual drug discovery is required to combat genetic diseases, life style threats and infectious diseases.

Prophetical Example 1

Enhancement of Inducible Expression System

As discussed above, Applicants have demonstrated specific examples of improved methods and systems for producing fungal secondary metabolites.

Applicants envision that one could enhance the inducible system as discussed above or similar that will allow simultaneous and specific co-expression of all biosynthetic enzyme-encoding genes of any fungal gene cluster.

Specifically, one could construct a new *A. nidulans* strain harboring a dominant-active copy of the transcriptional enhancer AflR. The dominant active version of AflR could be achieved by site directed mutation of certain amino acids uncoupling AflR from post-transcriptional control mechanisms. Inducibility of aflR expression could be achieved by fusion to the nitrate inducible promoter as described above. This construct will allow genes to be both inducible and of highest expression when induced. The reasoning for using an inducible system is that many fungal SMs have significant biological effects on fungi including fungicidal properties and thus the ability to induce a SM cluster at a time point when the fungus can withstand potential detrimental impacts is important.

Typically, young cultures such as germinating spores are not able to survive appreciable amounts of toxic metabolites, whereas cultures that have reached the exponential growth phase are able to continue growth to accumulate the metabolites of interest in large amounts. So far no set of inducible promoters is available to specifically induce a whole gene cluster in a heterologous host. The construction of a new *A. nidulans* strain harboring the inducible mutated aflR gene that will enhance expression of ST promoter-fused genes will be integrated into the existing technology as discussed above, thereby providing a new mechanism for maximizing targeted gene expression.

Prophetical Example 2

Production of Known Fungal SMs

Applicants envision that one could use the enhanced technology as discussed above for the production of known fungal SMs with commercially value, e.g. lovastatin, penicillin, and gibberellins. Production of these metabolites could be quantified.

Those skilled in the art will recognize, or be able to ascertain using no more then routine experimentation, numerous equivalents to the specific polypeptides, nucleic acids, methods, assays and reagents described herein. Such equivalents are considered to be within the scope of this invention and covered by the following claims. All publications, patents, and patent applications cited herein are hereby incorporated by reference in their entirety for all purposes.

This application includes a sequence listing that is submitted herewith in computer readable form (CRF). The CRF version of the sequence listing is incorporated by reference herein in its entirety,

REFERENCES

1. Shimizu, K., Hicks, J. K., Huang, T. P. & Keller, N. P. Pka, Ras and RGS protein interactions regulate activity of AflR, a Zn(II)2Cys6 transcription factor in *Aspergillus nidulans*. Genetics 165, 1095-1104 (2003).
2. Wiemann, P. et al. Biosynthesis of the red pigment bikaverin in *Fusarium fujikuroi*: genes, their function and regulation. Mol Microbiol 72, 931-946 (2009).
3. Brown, D. W. et al. Twenty-five coregulated transcripts define a sterigmatocystin gene cluster in *Aspergillus nidulans*. Proc Natl Acad Sci USA 93, 1418-1422 (1996).
4. Yu, J. H. et al. Conservation of structure and function of the aflatoxin regulatory gene aflR from *spergillus nidulans* and *A. flavus*. Curr Genet 29, 549-555 (1996).
5. Johnstone, I. L. et al. Isolation and characterisation of the crnA-niiA-niaD gene cluster for nitrate assimilation in *Aspergillus nidulans*. Gene 90, 181-192 (1990).

The invention claimed is:

1. A genetically modified *Aspergillus nidulans* for producing one or more secondary metabolites comprising:
an *Aspergillus nidulans* organism comprising an engineered gene cluster comprising the *A. nidulans* sterigmatocystin gene cluster transcriptional enhancer genes aflR and aflJ operably linked to a nitrate-inducible promoter, wherein none of the other genes included in the wild type *A. nidulans* sterigmatocystin gene cluster are present in the engineered gene cluster;
wherein the genetically modified *A. nidulans* is capable of nitrate-induced expression of the aflR and aflJ gene products.

2. The genetically modified *Aspergillus nidulans* of claim 1, wherein the wild type *A. nidulans* sterigmatocystin gene cluster is not present, and wherein the engineered gene cluster is inserted where the wild type *A. nidulans* sterigmatocystin gene cluster normally occurs.

3. The genetically modified *Aspergillus nidulans* of claim 1, wherein the nitrate-inducible promoter is niiA/niaD.

4. The genetically modified *Aspergillus nidulans* of claim 1, further comprising an exogenous expression vector comprising one or more *A. nidulans* sterigmatocystin gene cluster promoters operably linked to one or more protein-encoding genes, wherein the one or more *A. nidulans* sterigmatocystin gene cluster promoters are inducible by AflR/AflJ.

5. The genetically modified *Aspergillus nidulans* of claim 1, wherein the genetically modified *A. nidulans* is strain TPMW2.3.

6. The genetically modified *Aspergillus nidulans* of claim 1, wherein the nitrate-inducible promoter is repressible by ammonium.

7. The genetically modified *Aspergillus nidulans* of claim 4, wherein the one or more protein-encoding genes are from a fungal secondary metabolite gene cluster, and wherein the genetically modified *A. nidulans* is capable of nitrate-induced expression of the secondary metabolite.

8. The genetically modified *Aspergillus nidulans* of claim 7, wherein the exogenous expression vector comprises a fungal secondary metabolite gene cluster.

9. The genetically modified *Aspergillus nidulans* of claim 4, wherein the proteins encoded by the protein-encoding genes are biosynthetic enzymes.

10. An expression vector for producing fungal secondary metabolites, comprising one or more *Aspergillus nidulans* sterigmatocystin gene cluster promoters operably linked to one or more protein-encoding genes that are not part of the *A. nidulans* sterigmatocystin gene cluster, wherein the one or more *A. nidulans* sterigmatocystin gene cluster promoters are inducible by AflR/AflJ.

11. The expression vector of claim 10, comprising a fungal gene cluster other than the *Aspergillus nidulans* sterigmatocystin gene cluster.

12. The expression vector of claim 11, wherein the fungal gene cluster is a secondary metabolite gene cluster.

13. A kit for producing fungal secondary metabolites, the kit comprising:
(a) the genetically modified *Aspergillus nidulans* of claim 1; and
(b) the expression vector of claim 10.

14. A method for producing fungal secondary metabolites (SM), the method comprising contacting the genetically modified *Aspergillus nidulans* of claim 4 with nitrate, whereby one or more of the proteins encoded by the expression vector are expressed, and whereby a fungal secondary metabolite is produced.

15. The method of claim 14, further comprising the step of producing the genetically modified *Aspergillus nidulans* of claim 4 by transforming the genetically modified *A. nidulans* of claim 1 with the expression vector of claim 10.

16. The method of claim 14, wherein the strain of *Aspergillus nidulans* is *A. nidulans* strain TPMW23.

* * * * *

SEQUENCE LISTING

```
<160> NUMBER OF SEQ ID NOS: 7

<210> SEQ ID NO 1
<211> LENGTH: 7162
<212> TYPE: DNA
<213> ORGANISM: Artificial Sequence
<220> FEATURE:
<223> OTHER INFORMATION: Engineered pWhite plasmid

<400> SEQUENCE: 1
ctctggaaca gtctcgccgt cttgctcgtg catttgacca agccacttt  caggtggctt    60 ttggtccctc atgatttacg aatgattcaa gcaggaaatc tcttgttgag cgaggagtct   120
ctcggcagtg atgacgtcta ttgtagagcc tccatgcagt cggctcgaga atgtaaccta   180
atgaaagaca accaattcaa cggatacca ctacgctgaa tagtgctgac tggtacgatc    240
gcatttgctc aggtcaagct tagatcaagg atcataatca gtgctctcaa tgaccgatcc   300
atcgacgagg cccaatagat agtagatata gcttgttttt cgatatgatg gtgacacgtg   360
acgccagctc tcttcccttt ccggaacaca tgcaaagaac ttgattttga gacctaccgg   420
gagcgtcgca atcaaatctg ttgaatttct cttcgactca tgttccttga ttctcaggtt   480
tttgttgcta tcgggccgat gcataacaag gtcaatctat ccgtccagca cattcctaga   540
acaatcatcg ggaatccgaa cgagtgttgg acccgaaaac agaccgttgc ctctttcatc   600
atgacggaag ccctgcaagg ctgaagcaca gttaggatta gtggaagagt tccacttggt   660
tcccaagact gattccgatc tagatctttc cattcatgaa tcgaccaaat aggagccttg   720
```

-continued

```
cgtgatggcc cacaaaacag tgagggttgt attcgaacaa cctgattaga acggcttgcc    780
gatgctacat tgcctacgat ccaggaatag cacagagatg tacggagcgg actcgaagta    840
tgttgcaacc aggtatagga agtgggccac ctcgcgaaaa ggcaaaaagg actgcatcag    900
tataaaagtc tgctcataga agatcgcggc gtattccgcc gctgattctg ggatgaactc    960
aattgcctga tcagcggact tgactctcct tctcctgatc gctagcgaga gttattctgt   1020
gtctgacgaa atatgttgtg tatatatata tatgtacgtt aaaagttccg tggagttacc   1080
agtgattgac caatgtttta tcttctacag ttctgcctgt ctaccccatt ctagctgtac   1140
ctgactacag agtagtttaa ttgtggttga ccccacagtc ggaggcggag gaatacagca   1200
ccgatgtggc ctgtctccat ccagattggc acgcaatttt tacacgcgga aaagatcgag   1260
atagagtacg actttaaatt tagtccccgg cggcttctat tttagaatat ttgagatttg   1320
attctcaagc aattgatttg gttgggtcac cctcaattgg ataatatacc tcattgctcg   1380
gctacttcaa ctcatcaatc accgtcatac cccgcatata accctccatt cccacgatgt   1440
cgtccaagtc gcaattgact tacggtgctc gagccagcaa gcaccccaat cctctggcaa   1500
agagactttt tgagattgcc gaagcaaaga agacaaacgt taccgtctct gctgatgtga   1560
cgacaacccg agaactcctg gacctcgctg accgtacgga agctgttgga tccaatacat   1620
atgccgtcta gcaatggact aatcaacttt tgatgataca ggtctcggtc cctacatcgc   1680
cgtcatcaag acacacatcg acatcctcac cgatttcagc gtcgacacta tcaatggcct   1740
gaatgtgctg gctcaaaagc acaactttt gatcttcgag gaccgcaaat tcatcgacat   1800
cggcaatacc gtccagaagc aataccacgg cggtgctctg aggatctccg aatgggccca   1860
cattatcaac tgcagcgttc tccctggcga gggcatcgtc gaggctctgg cccagaccgc   1920
atctgcgcaa gacttcccct atggtcctga gagaggactg ttggtcctgg cagagatgac   1980
ctccaaagga tcgctggcta cgggcgagta taccaaggca tcggttgact acgctcgcaa   2040
atacaagaac ttcgttatgg gtttcgtgtc gacgcgggcc ctgacggaag tgcagtcgga   2100
tgtgtcttca gcctcggagg atgaagattt cgtggtcttc acgacgggtg tgaacctctc   2160
ttccaaagga gataagcttg gacagcaata ccagactcct gcatcggcta ttggacgcgg   2220
tgccgacttt atcatcgccg gtcgaggcat ctacgctgct cccgacccgg ttgaagctgc   2280
acagcggtac cagaaagaag gctgggaagc ttatatggcc agagtatgcg gcaagtcatg   2340
atttcctctt ggagcaaaag tgtagtgcca gtacgagtgt tgtggaggaa ggctgcatac   2400
attgtgcctg tcattaaacg atgagctcgt ccgtattggc ccctgtaatg ccatgttttc   2460
cgcccccaat cgtcaaggtt ttcccttgt tagattccta ccagtcatct agcaagtgag   2520
gtaagctttg ccagaaacgc caaggcttta tctatgtagt cgataagcaa agtggactga   2580
tagcttaata tggaaggtcc ctcaggacaa gtcgacctgt gcagaagaga taacagcttg   2640
gcatcacgca tcagtgcctc ctctcagaca gaatgcggcc gcatgacgcg aatcacttta   2700
ctatgacaaa gggcgaaaag gcaaggagc ttgctacttt catgaagaat gcgttggggg   2760
tttgtgagcg ccggttggtc tgataatgtc aatttgtttg ctttggtttt ggcttaggtt   2820
ttgatccatt aatgctattc tattgttgct cataaggttt tactttcccg tttcatcttg   2880
tactctaaac ataaagggta aacaataata atcctctggt tctaatataa aggttcttga   2940
gagactgcat ctaagtgttc agccacaatc aattgcgata ctctatttcc tagctattta   3000
acgcccaaag ttttggaaac ccggacaata gtgcgaacaa cccaactagt agccgcggta   3060
```

```
taaacggtgt cgcataaaaa gagcaaatgt acactagcat tgcagtcaaa acaaccctgg   3120
gtcaatgcaa tgtcataatt cataaagggc cgcaatatga tgacatgctg tagtcgtcta   3180
agcaagtgaa ggcatgtaag gtagtagtag gcacggtaac atccagtttc agcactccct   3240
gtaaacgtca tagagtgtct ggcagtgggg aagaggccc  aagaaaccca gtccaacgtc   3300
aaatctgaac agaaaagatt tcagaaggat aggactttcc gtgagctttc cactcagaaa   3360
aacccggaag atgaatggat tgctctggtt tgtattgatc gattgaagta aaacttaatt   3420
gagagaggag gcatatggta tgtaggcgcg acgggtttat tcatagggac atctcagaac   3480
taaacctaag agcgcttccg cggcctggaa aattagatcc gttattattg attccagggc   3540
ttgtaggacg gctgtagttg ttcgcattta actttgggct tcgtggttgg gtgcttgttg   3600
agcgtgtgga tgggcgattc ttgcggatct cgcggagctc gtcctctttc ttctggagga   3660
gatcttcgcg tactgacagc acaggggata acgcaggaaa gaacatgtga gcaaaaggcc   3720
agcaaaaggc cagcaaaagg ccaggaaccg taaaaaggcc gcgttgctgg cgttttccca   3780
taggctccgc ccccctgacg agcatcacaa aaatcgacgc tcaagtcaga ggtggcgaaa   3840
cccgacagga ctataaagat accaggcgtt tccccctgga agctccctcg tgcgctctcc   3900
tgttccgacc ctgccgctta ccggatacct gtccgccttt ctcccttcgg gaagcgtggc   3960
gctttctcat agctcacgct gtaggtatct cagttcggtg taggtcgttc gctccaagct   4020
gggctgtgtg cacgaacccc ccgttcagcc cgaccgctgc gccttatccg gtaactatcg   4080
tcttgagtcc aacccggtaa gacacgactt atcgccactg gcagcagcca ctggtaacag   4140
gattagcaga gcgaggtatg taggcggtgc tacagagttc ttgaagtggt ggcctaacta   4200
cggctacact agaaggacag tatttggtat ctgcgctctg ctgaagccag ttaccttcgg   4260
aaaaagagtt ggtagctctt gatccggcaa acaaaccacc gctggtagcg gtggttttt   4320 tgtttgcaag cagcagatta cgcgcagaaa aaaggatct  caagaagatc ctttgatctt   4380
ttctacgggg tctgacgctc agtggaacga aaactcacgt taagggattt tggtcatgag   4440
attatcaaaa aggatcttca cctagatcct tttaaattaa aaatgaagtt ttaaatcaat   4500
ctaaagtata tatgagtaaa cttggtctga cagttaccaa tgcttaatca gtgaggcacc   4560
tatctcagcg atctgtctat ttcgttcatc catagttgcc tgactccccg tcgtgtagat   4620
aactacgata cgggagggct taccatctgg ccccagtgct gcaatgatac cgcgagaccc   4680
acgctcaccg gctccagatt tatcagcaat aaaccagcca gccggaaggg ccgagcgcag   4740
aagtggtcct gcaactttat ccgcctccat ccagtctatt aattgttgcc gggaagctag   4800
agtaagtagt tcgccagtta atagtttgcg caacgttgtt gccattgctg caggcatcgt   4860
ggtgtcacgc tcgtcgtttg gtatggcttc attcagctcc ggttcccaac gatcaaggcg   4920
agttacatga tcccccatgt tgtgcaaaaa agcggttagc tccttcggtc ctccgatcgt   4980
tgtcagaagt aagttggccg cagtgttatc actcatggtt atggcagcac tgcataattc   5040
tcttactgtc atgccatccg taagatgctt ttctgtgact ggtgagtact caaccaagtc   5100
attctgagaa tagtgtatgc ggcgaccgag ttgctcttgc ccggcgtcaa cacgggataa   5160
taccgcgcca catagcagaa ctttaaaagt gctcatcatt ggaaaacgtt cttcggggcg   5220
aaaactctca aggatcttac cgctgttgag atccagttcg atgtaaccca ctcgtgcacc   5280
caactgatct tcagcatctt ttactttcac cagcgtttct gggtgagcaa aaacaggaag   5340
gcaaaatgcc gcaaaaaagg gaataagggc gacacgaaaa tgttgaatac tcatactctt   5400 ccttttttcaa tattattgaa gcatttatca gggttattgt ctcatgagcc attatacgaa   5460
```

```
gttatgcacc acgctttta attcaattca tcattttttt tttattcttt tttttgattt    5520
cggtttcctt gaattttttt tgattcggta atctccgaac agaaggaaga acgaaggaag    5580
gagcacagac ttagattggt atatatacgc atatgtagtg ttgaagaaac atgaaattgc    5640
ccagtattct taacccaact gcacagaaca aaaacctgca ggaaacgaag ataaatcatg    5700
tcgaaagcta catataagga acgtgctgct actcatccta gtcctgttgc tgccaagcta    5760
tttaatatca tgcacgaaaa gcaaacaaac ttgtgtgctt cattggatgt tcgtaccacc    5820
aaggaattac tggagttagt tgaagcatta ggtcccaaaa tttgtttact aaaaacacat    5880
gtggatatct tgactgattt ttccatggag ggcacagtta agccgctaaa ggcattatcc    5940
gccaagtaca attttttact cttcgaagac agaaaatttg ctgacattgg taatacagtc    6000
aaattgcagt actctgcggg tgtatacaga atagcagaat gggcagacat tacgaatgca    6060
cacggtgtgg tgggcccagg tattgttagc ggtttgaagc aggcggcaga agaagtaaca    6120
aaggaaccta gaggcctttt gatgttagca gaattgtcat gcaagggctc cctatctact    6180
ggagaatata ctaagggtac tgttgacatt gcgaagagcg acaaagattt tgttatcggc    6240
tttattgctc aaagagacat gggtggaaga gatgaaggtt acgattggtt gattatgaca    6300
cccggtgtgg gtttagatga caagggagac gcattgggtc aacagtatag aaccgtggat    6360
gatgtggtct ctacaggatc tgacattatt attgttggaa gaggactatt tgcaaaggga    6420
agggatgcta aggtagaggg tgaacgttac agaaaagcag gctgggaagc atatttgaga    6480
agatgcggcc agcaaaacta aaaaactgta ttataagtaa atgcatgtat actaaactca    6540
caaattagag cttcaattta attatatcag ttattaccca taacttcgta tagcatacat    6600
tatacgaagt tatcccgggt accgagctcg aattcgtaac ttacacgcgc tcgtatctt    6660 ttaatgatgg aataatttgg gaattactc tgtgtttatt tatttttatg ttttgtattt    6720
ggattttaga aagtaaataa agaaggtaga agagttacgg aatgaagaaa aaaaaataaa    6780
caaaggttta aaaaatttca acaaaaagcg tactttacat atatatttat tagacaagaa    6840
aagcagatta aatagatata cattcgatta acgataagta aaatgtaaaa tcacaggatt    6900
ttcgtgtgtg gtcttctaca cagacaagat gaaacaattc ggcattaata cctgagagca    6960
ggaagagcaa gataaaaggt agtatttgtt ggcgatcccc ctagagtctt ttacatcttc    7020
ggaaaacaaa actatttttt tctttaattt cttttttttac tttctatttt taatttatat    7080
atttatatta aaaatttaa attataatta ttttatagc acgtgatgaa ttcgtaatca    7140
tggtcatagc tgtttcctgt gt    7162
```

<210> SEQ ID NO 2
<211> LENGTH: 9886
<212> TYPE: DNA
<213> ORGANISM: Artificial Sequence
<220> FEATURE:
<223> OTHER INFORMATION: Engineered pYellow plasmid

<400> SEQUENCE: 2

```
gatggagatt ggcgccgttc tttatctgtt gtgccaccag tctctttaaa catcagaaac    60
gtcgggccag atgtagaatc ggccacggac ctgacaattc tcgacgtctc tgagatcccc    120
gacaagtttc tcagtggagc gaatgaagga ttcaacgaag cccacacccg ctttctcgag    180
gttctccgcc tagctggtgg gttgaaccgc ttactcagtg tcgaaggat aaatgagatc    240 aatttctccc gtgaagccat tcagcaaggt atccatgcgg ctctcgtgga acacaatgct    300
```

```
aacgccctca ccaccctcct taagctcgac gagtttacct tccgttgcca gaacaacctt    360
gtagatgccg tgtataccct accaccagag catttccgca ccgctgtccg tgtggcacga    420
cacgactcta gcttcttcca gcttctgctg cgtgcgagtg ctgagtctgt tccctacgac    480
gattcggaga tcacgcactg ggcagttact acgggtggtc cttttgaaca atggctactg    540
gatttcatgc tgcagctgcc ggagcaaatc agggcgacaa ccaagggaag tcaacaaatg    600
ttctatcatg ggggcttgaa tacagcaagt gccatgacag aaaggtatct tcgagatatt    660
ctgggaacgg atgagcttaa ggtctggcta aagagtcgt cgtacgattt tcccagcgaa    720
tggattgttg agagttgatg ttgaagatat tgaacaaatt tctgtggtga tgagcgctgg    780
aagaatcagt gtacaacgaa aggagcagac aagactccct tgctatactc aggtgtgaca    840
cctgcaaatc cagtaggaaa atacggtaat taatcccagg gtcttttccc tccgccaggc    900
accacgcccc ttgccggaaa cgtcgcgcag tcgcgttcag caccaggtac attccaatca    960
acaatgcaag aatgtgaaac gcgaagtata tatcagcgaa caacatcaag ccgacaggcg   1020
cgccgcggac tgagttatgg atgactccct ttcgatgata ccctttagca gaagtgttct   1080
taaattgcgg gaagaggccg ttcaggagtc tggctcgttt gatcacatgg gattaaaata   1140
tggtgttgag gctgggatat tttatgtttt gtctcttgcg cttcgatatc aacagattga   1200
caataatgaa taactatcta cggactatga atgcagctcg atctactccg tatttagtcg   1260
ggcaatctcc cgtagaagat gctagactgc gctgaaagac taggcacagt taattgccgc   1320
ggatcacgtc aggcctgaca aatgacaggt ggaccttcat gtaatcgcac gatgagtcag   1380
cgcctcttct cccccgccga cttgcagctg cggatgtccc gaggagccga acattgaatc   1440
tatcccaaga gtgactgaaa tatgattgca atcgtcgtct ttttcttgca gagaatgtgg   1500
tgaggtgatc aatcgtgttt ttcttcatat attatattct gtaatgatca tacttttgttg   1560
agatacccgt ctctaaaatt gtactttcgc ctccctcctc cctctcaagt ccgtcatcgc   1620
aatgtcgaat ttaccgtccc atgcttctcc gtcttttggg gcgcaaacgc ctaccacgcc   1680
gcagcccgtc gacgagcttt ctctcaagtc gaacatcaca tcagcccctg cgttacactc   1740
cagattagac gaactccgag atgagacttc cagccagatc agcagcatag acactgaccg   1800
cggggacatg acccctgcgg ttccgcatc attactctcc ccatccttca ctcctccagc   1860
aaccccgggg ggctcgatca ataccgcgga gctgcttcaa cagacccaat tagctggcgc   1920
acggcaaggg tcaacacata ctaagccccc gaggttgctt tctcgtcttc ccaatgtcga   1980
atgtatcgtc cgcgctcgga tacccacgac aactggcgcg agatgtttc ttcacctgta   2040
ccacaatgac ttagacaaca aagagcattt ggcgattgtg tttggaaata caattcgaag   2100
cagaagcttg gacaagatcc ggcctggaga gacggagatg gatcgcatga tccgtggcgc   2160
gtatgtcggg aaactccgac cgggccgtgt gagcagctgg tatgacgagg agaaagctga   2220
agaggccgcc agtccggaag ctggcggcgc tgtatccagt ccgcacacac tgccgcgaag   2280
tagcctcaag gaggcacctc ttgtgagaat ccattcggag tgctacactg gtgagacggc   2340
ttggtctgca cgctgcgact gcggcgagca gctcgatgaa gcagctcgcc tcatgtcgct   2400
gcctatggaa acgttggcag aggctgcgtc accgccggat ggggcggtac cgtcaaatgc   2460
tgctggaggt gtaattgtgt acctgcgcca agaaggacga ggcattgggc tgggcgagaa   2520
actgaaagcg tacaatcttc aggatctggg atcagacacg gtggaagcca atctcctgct   2580
tcgccaccct gcggatgcaa gaagttatgg attagctacg gcgatcctgg tggatcttgg   2640
tctagggatt gactcgaatc cgcacggcat ccgactactc acgaataacc cggacaagat   2700
```

```
tcgagcggtt gagggaccca accgagaagt ggtggtgaaa gagcgggtgc cgatggtgcc    2760
attggcatgg agatcgggtg gaaagatggg aatcaagagt tccgaggtcg aagggtatct    2820
gagaacgaag gtatgtcgac aatctatctc ttgcaagcta gcttattttc tcatcattct    2880
taaacaatgt ctcactctct cctcgcagat atcgaaaatg gccatttgc tccaatgaac    2940 ctatccccctt tcggttagta accttgtgct ggaagtacgc cttcctgctt ttggacttag    3000
ccaagtcgac acggtgtatg ctcgtcacac tcatgtaacg gttctgcagc gcaaacgttc    3060
tggtcacgtt attcgctttt gtccattttg tcttttttgtg cggtacataa actagaggat    3120
tagcgcactt tgtacatgat gttcccgaca tgtcacatta ggcctcgatt ggtcaaaata    3180
atccctctct aacctctggt tcgcatactc ttaaatgcag ctctagtctc tagacggact    3240
agttcctcct gcagtggatg tctgacgagt gtctgcaagg accgttttcc gtgtccagtt    3300
agttccaatc acccggatat cggcgagacg tcggccgatt gagatcactg agtcaatggc    3360
gttgagtggc acttgttgga cggggttgat gtttgggatt cttaggtgag ctctcatatt    3420
cgtacttaca agatgtttgt tctaaaatta tttaataatt attttttaat ctctatgaaa    3480
tggagaagct ttttttttctc tcttttttgg cttctttaaa ttatatcagc atatttatta    3540
aatcattgga actctagatg tacgccccag agaagtagaa ctacatattc ccaatcaacc    3600
tcagaatacc tctgaccctc ccagccagcg tgatctgata ccccgtctca acaacccccct   3660 tgcacatctc aaatgcacca tccccattct ctttctccgc ttctcccttc ataatcggat    3720
aatccacgcg cggcggaatc ctcgtcgcca taaggcgcgg gaacctgtca acgcaaatcg    3780
ctttgatatt acttacgccc cgcagacctt cttcgcccgc aaaccggcca tacccagatc    3840
ccttgacgcc gccgaatggc agctgtactg tgtagtagct gccaaaatcg ttaacagaga    3900
ccatgcctgc ctttattcct gagacacaag cattcacgtc gcgcgtgttg tagccaaata    3960
ccgaggcacc tagcgcgtat tgggtagaat ttgcgatggt gattgcgtcg gagacggaag    4020
atgcacgcat catgaggaag acgggggcga agagctctgt ttgggcaatt tccatggagg    4080
gcgtgacgtc tgcaaggagg gtcggtgtga aatagtgacc gagcggatag gttgggtgtt    4140
cgaattgttt cccaccagcg acgaggcgag caccttggct gacggcgcgc tgaatgagaa    4200
actccaagcg ggagaaagag gccggggaga tcatggcccc cacgtctggg gcacctgact    4260
tgttgtttgg gttgttgggc tttgtgtcta gtaagactga accgaggcgg agggctttaa    4320
tgcgggaggt gacggtgtca aggagtttgt cgtatacgcc agggagggca atgacgcgct    4380
caacgccgat agctcgaatt cactggccgt cgttttacaa cgtcgtgact gggaaaaccc    4440
tggcgttacc caacttaatc gccttgcagc acatccccct ttcgccagct ggcgtaatag    4500
cgaagaggcc cgcaccgatc gcccttccca acagttgcgc agcctgaatg gcgaatggcg    4560
cctgatgcgg tattttctcc ttacgcatct gtgcggtatt tcacaccgca tatatcggat    4620
cgtacttgtt acccatcatt gaattttgaa catccgaacc tggagttttt ccctgaaaca    4680
gatagtatat ttgaacctgt ataataatat atagtctagc gctttacgga agacaatgta    4740
tgtatttcgg ttcctggaga aactattgca tctattgcat aggtaatctt gcacgtcgca    4800
tccccggttc attttctgcg tttccatctt gcacttcaat agcatatctt tgttaacgaa    4860
gcatctgtgc ttcattttgt agaacaaaaa tgcaacgcga gagcgctaat ttttcaaaca    4920
aagaatctga gctgcatttt tacagaacag aaatgcaacg cgaaagcgct attttaccaa    4980
cgaagaatct gtgcttcatt tttgtaaaac aaaaatgcaa cgcgagagcg ctaattttttc    5040
```

```
aaacaaagaa tctgagctgc attttttacag aacagaaatg caacgcgaga gcgctatttt   5100
accaacaaag aatctatact tctttttttgt tctacaaaaa tgcatcccga gagcgctatt   5160
tttctaacaa agcatcttag attacttttt ttctcctttg tgcgctctat aatgcagtct   5220
cttgataact ttttgcactg taggtccgtt aaggttagaa aaggctact ttggtgtcta    5280
ttttctcttc cataaaaaaa gcctgactcc acttcccgcg tttactgatt actagcgaag   5340
ctgcgggtgc attttttcaa gataaaggca tccccgatta tattctatac cgatgtggat   5400
tgcgcatact ttgtgaacag aaagtgatag cgttgatgat tcttcattgg tcagaaaatt   5460
atgaacggtt tcttctattt tgtctctata tactacgtat aggaaatgtt tacatttttcg  5520
tattgttttc gattcactct atgaatagtt cttactacaa ttttttttgtc taaagagtaa  5580
tactagagat aaacataaaa aatgtagagg tcgagtttag atgcaagttc aaggagcgaa   5640
aggtggatgg gtaggttata tagggatata gcacagagat atatagcaaa gagatacttt   5700
tgagcaatgt ttgtggaagc ggtattcgca atattttagt agctcgttac agtccggtgc   5760
gttttttggtt ttttgaaagt gcgtcttcag agcgcttttg gttttcaaaa gcgctctgaa  5820
gttcctatac tttctagcta gagaatagga acttcggaat aggaacttca aagcgtttcc   5880
gaaaacgagc gcttccgaaa atgcaacgcg agctgcgcac atacagctca ctgttcacgt   5940
cgcacctata tctgcgtgtt gcctgtatat atatatacat gagaagaacg gcatagtgcg   6000
tgtttatgct taaatgcgta cttatatgcg tctatttatg taggatgaaa ggtagtctag   6060
tacctcctgt gatattatcc cattccatgc ggggtatcgt atgcttcctt cagcactacc   6120
ctttagctgt tctatatgct gccactcctc aattggatta gtctcatcct tcaatgctat   6180
catttccttt gatattggat cgatccgatg ataagctgtc aaacatgaga attgggtaat   6240
aactgatata attaaattga agctctaatt tgtgagttta gtatacatgc atttacttat   6300
aatacagttt tttagtttttg ctggccgcat cttctcaaat atgcttccca gcctgctttt   6360
ctgtaacgtt cacctctac cttagcatcc cttcccttttg caaatagtcc tcttccaaca   6420
ataataatgt cagatcctgt agagaccaca tcatccacgg ttctatactg ttgacccaat   6480
gcgtctccct tgtcatctaa acccacaccg ggtgtcataa tcaaccaatc gtaaccttca   6540
tctcttccac ccatgtctct ttgagcaata aagccgataa caaaatcttt gtcgctcttc   6600
gcaatgtcaa cagtaccctt agtatattct ccagtagata gggagcccctt gcatgacaat   6660
tctgctaaca tcaaaaggcc tctaggttcc tttgttactt cttctgccgc ctgcttcaaa   6720
ccgctaacaa tacctgggcc caccacaccg tgtgcattcg taatgtctgc ccattctgct   6780
attctgtata caccccgcaga gtactgcaat tgactgtat taccaatgtc agcaaatttt    6840
ctgtcttcga agagtaaaaa attgtacttg gcggataatg cctttagcgg cttaactgtg   6900
ccctccatgg aaaaatcagt caagatatcc acatgtgttt ttagtaaaca aattttggga   6960
cctaatgctt caactaactc cagtaattcc ttggtggtac gaacatccaa tgaagcacac   7020
aagtttgttt gcttttcgtg catgatatta aatagcttgg cagcaacagg actaggatga   7080
gtagcagcac gttccttata tgtagctttc gacatgattt atcttcgttt cctgcatgtt   7140
tttgttctgt gcagttgggt taagaatact gggcaatttc atgtttcttc aacactacaa   7200
atgcgtatat ataccaatct catgtttctt caacactaca aatgcgtata taccaatc     7260
taagtctgtg ctccttcctt cgttcttcct tctgttcgga gattaccgaa tcaaaaaaat   7320
ttcaaagaaa ccgaaatcaa aaaaagaat aaaaaaaaaa tgatgaattg aattgaaaag    7380
ctaattcttg aagacgaaag ggcctcgtga tacgcctatt tttataggtt aatgtcatga   7440
```

```
taataatggt ttcttagacg tcaggtggca ctttttcgggg aaatgtgcgc ggaaccccta    7500
tttgtttatt tttctaaata cattcaaata tgtatccgct catgagacaa taaccctgat    7560
aaatgcttca ataatattga aaaggaaga gtatgagtat tcaacatttc cgtgtcgccc     7620 ttattcccctt ttttgcggca ttttgccttc ctgtttttgc tcacccagaa acgctggtga   7680
aagtaaaaga tgctgaagat cagttgggtg cacgagtggg ttacatcgaa ctggatctca    7740
acagcggtaa gatccttgag agttttcgcc ccgaagaacg ttttccaatg atgagcactt    7800
ttaaagttct gctatgtggc gcggtattat cccgtattga cgccgggcaa gagcaactcg    7860
gtcgccgcat acactattct cagaatgact tggttgagta ctcaccagtc acagaaaagc    7920
atcttacgga tggcatgaca gtaagagaat tatgcagtgc tgccataacc atgagtgata    7980
acactgcggc caacttactt ctgacaacga tcggaggacc gaaggagcta accgcttttt    8040
tgcacaacat gggggatcat gtaactcgcc ttgatcgttg ggaaccggag ctgaatgaag    8100
ccataccaaa cgacgagcgt gacaccacga tgcctgtagc aatggcaaca acgttgcgca    8160
aactattaac tggcgaacta cttactctag cttcccggca acaattaata gactggatgg    8220
aggcggataa agttgcagga ccacttctgc gctcggccct tccggctggc tggtttattg    8280
ctgataaatc tggagccggt gagcgtgggt ctcgcggtat cattgcagca ctggggccag    8340
atggtaagcc ctcccgtatc gtagttatct acacgacggg gagtcaggca actatggatg    8400
aacgaaatag acagatcgct gagataggtg cctcactgat taagcattgg taactgtcag    8460
accaagttta ctcatatata ctttagattg atttaaaact tcatttttaa tttaaaagga    8520
tctaggtgaa gatcctttt gataatctca tgaccaaaat cccttaacgt gagttttcgt     8580
tccactgagc gtcagacccc gtagaaaaga tcaaaggatc ttcttgagat cctttttttc    8640
tgcgcgtaat ctgctgcttg caaacaaaaa aaccaccgct accagcggtg gtttgtttgc    8700
cggatcaaga gctaccaact ctttttccga aggtaactgg cttcagcaga gcgcagatac    8760
caaatactgt ccttctagtg tagccgtagt taggccacca cttcaagaac tctgtagcac    8820
cgcctacata cctcgctctg ctaatcctgt taccagtggc tgctgccagt ggcgataagt    8880
cgtgtcttac cgggttggac tcaagacgat agttaccgga taaggcgcag cggtcgggct    8940 gaacggggggg ttcgtgcaca cagcccagct tggagcgaac gacctacacc gaactgagat    9000
acctacagcg tgagctatga gaaagcgcca cgcttcccga agggagaaag gcggacaggt    9060
atccggtaag cggcagggtc ggaacaggag agcgcacgag ggagcttcca gggggaaacg    9120
cctggtatct ttatagtcct gtcgggtttc gccacctctg acttgagcgt cgatttttgt    9180
gatgctcgtc agggggggcgg agcctatgga aaaacgccag caacgcggcc ttttttacggt   9240 tcctggcctt ttgctggcct tttgctcaca tgttctttcc tgcgttatcc cctgattctg    9300
tggataaccg tattaccgcc tttgagtgag ctgataccgc tcgccgcagc cgaacgaccg    9360
agcgcagcga gtcagtgagc gaggaagcgg aagagcgccc aatacgcaaa ccgcctctcc    9420
ccgcgcgttg gccgattcat taatgcagct ggcacgacag gtttcccgac tggaaagcgg    9480
gcagtgagcg caacgcaatt aatgtgagtt agctcactca ttaggcaccc caggctttac    9540
actttatgct tccggctcgt atgttgtgtg gaattgtgag cggataacaa tttcacacag    9600
gaaacagcta tgaccatgat tacgccaagc ttgcatgcct gcaggtcgac tctagaggat    9660
ccccctggca cgacaggttt cccgactgga aagcgggcag tgagcgcaac gcaattaatg    9720
tgagttagct cactcattag gcaccccagg ctttacactt tatgcttccg gctcgtatgt    9780
```

```
tgtgtggaat tgtgagcgga taacaatttc acacaggaaa cagctatgac catgattacg   9840
ccaagctcga aattaaccct cactaaaggg aacaaaagct ggagct                   9886

<210> SEQ ID NO 3
<211> LENGTH: 365
<212> TYPE: DNA
<213> ORGANISM: Aspergillus nidulans

<400> SEQUENCE: 3
tggactcgca atcagagggg acaatctgc atcatgaatt ccccttctgt tggaacgcct     60
gatatagtac gcttgtgcgg ttgaccccag tgtatcgggc actcaaccgg tcatctattc   120
ttgactcggt gaagagagac tgcaatcggc agatgctcgg gtatcgctaa agaatactct   180
gtcctcttcc cagtaaaccc cggtacagtc agcgacggat cacggtcagc gaggccatga   240
ccgactcggc agctccttga ttgacacctt gcacatgtaa gataaaatag gcaatctgaa   300
tctcaccgtt agcttagaat catggaactg cagaccatac tattttcgca ataaacggct   360
ccagg                                                                365

<210> SEQ ID NO 4
<211> LENGTH: 192
<212> TYPE: DNA
<213> ORGANISM: Aspergillus nidulans

<400> SEQUENCE: 4
actgaggact caggggggta gctaagtggg ctgcagacgg atcagataca ataacgccat     60
acgttatggt ggacatttac cagacggatg aagatccaat taagaacatt gtagctcggt   120
gaccgacatt caacataaga caaatcgaac ctcgcgatga aagtccgtag cagacaacag   180
atcgcttcaa ca                                                        192

<210> SEQ ID NO 5
<211> LENGTH: 209
<212> TYPE: DNA
<213> ORGANISM: Aspergillus nidulans

<400> SEQUENCE: 5
ggttttgaag agttccagga gtatgaactt atgcttgggg tatctgccag gtctcttttt     60
ctcgtcttat accgacgcct acatgggtct cggcaagcga tcggtgaggg ctccgccatg   120
tgccgaagta ttggtacgtg gtggccggtt tattaacttc gcgagagcct aagctacaga   180
cgagcaccat cagacagacc atcgtcact                                      209

<210> SEQ ID NO 6
<211> LENGTH: 159
<212> TYPE: DNA
<213> ORGANISM: Aspergillus nidulans

<400> SEQUENCE: 6
ggctactgca tgccattcta ttctggatca caatgtgcca atatttgtga tgtaatacta     60
gccccgaacc ccgaagcacg gtgaggctcg ctgagcgaag ccaaaatctt acattaagtc   120
cagatcttgg tggtgcaaat accctcacag aaccaaaca                           159

<210> SEQ ID NO 7
<211> LENGTH: 230
<212> TYPE: DNA
<213> ORGANISM: Aspergillus nidulans

<400> SEQUENCE: 7
```

-continued

```
attgttcttg ctgagtacag atatgatgct gttgagcagt tgttgaaccg tcaagacacg        60
cacttatagc catggacccc gctctgccaa cctgtcatgc aatgctcggc atgcgattaa       120
ccgactcgct ggccgaaccc tgactataat gtgtccatta tatgaacatt gggatatcta       180
aaggcgattc atatccgttt tagaccatac agcacacaat acccccgca                   230
```